US011780818B2

(12) United States Patent
Yemireddy et al.

(10) Patent No.: US 11,780,818 B2
(45) Date of Patent: Oct. 10, 2023

(54) METHODS OF MAKING DELMOPINOL AND SALTS THEREOF

(71) Applicant: You First Services, Inc., Buffalo, NY (US)

(72) Inventors: Venkataramana Reddy Yemireddy, Hyderabad (IN); Balraju Vadla, Hyderabad (IN); Vijaya Kumar Kongara, Hyderabad (IN); Vidya Sagar Gottam, Hyderabad (IN)

(73) Assignee: You First Services, Inc., Buffalo, NY (US)

( * ) Notice: Subject to any disclaimer, the term of this patent is extended or adjusted under 35 U.S.C. 154(b) by 0 days.

(21) Appl. No.: 17/759,850

(22) PCT Filed: Feb. 1, 2021

(86) PCT No.: PCT/US2021/016040
§ 371 (c)(1),
(2) Date: Jul. 29, 2022

(87) PCT Pub. No.: WO2021/155350
PCT Pub. Date: Aug. 5, 2021

(65) Prior Publication Data
US 2023/0094524 A1  Mar. 30, 2023

Related U.S. Application Data

(60) Provisional application No. 62/968,730, filed on Jan. 31, 2020.

(51) Int. Cl.
*C07D 265/30* (2006.01)
(52) U.S. Cl.
CPC .................................. *C07D 265/30* (2013.01)
(58) Field of Classification Search
CPC .................................................... C07D 265/30
See application file for complete search history.

(56) References Cited

U.S. PATENT DOCUMENTS

| | | | |
|---|---|---|---|
| 3,598,814 | A | 8/1971 | Reisner et al. |
| 5,155,220 | A | 10/1992 | Hernestam et al. |
| 5,212,305 | A | 5/1993 | Hernestam et al. |
| 7,902,357 | B2 | 3/2011 | Surroca et al. |
| 8,093,398 | B2 | 1/2012 | Comely et al. |
| 8,999,365 | B2 | 4/2015 | Lane et al. |
| 9,050,338 | B2 | 6/2015 | Arnebrant |
| 10,206,928 | B2 | 2/2019 | Attstrom et al. |
| 10,894,778 | B2 | 1/2021 | De Faveri et al. |
| 2011/0082301 | A1* | 4/2011 | Comely ............... C07D 309/04 548/215 |
| 2011/0092751 | A1 | 4/2011 | Surroca et al. |
| 2019/0388302 | A1 | 12/2019 | Schobel et al. |
| 2020/0345624 | A1 | 11/2020 | Hudson |
| 2020/0352851 | A1 | 11/2020 | Rynerson |
| 2021/0040051 | A1 | 2/2021 | De Faveri et al. |
| 2021/0130307 | A1 | 5/2021 | De Faveri et al. |

FOREIGN PATENT DOCUMENTS

| | | |
|---|---|---|
| WO | 2007057681 A1 | 5/2007 |
| WO | 2008017814 A1 | 2/2008 |
| WO | 2018115096 A1 | 6/2018 |
| WO | 2018115111 A1 | 6/2018 |
| WO | 2018115116 A1 | 6/2018 |
| WO | 2019038379 A1 | 2/2019 |

OTHER PUBLICATIONS

Pubchem CID 10901285, 4-[[(2S,3As)-2,3,3a,4,6,7-hexahydro-[1,2]oxazolo[3,2-c] [1,4]oxazin-2-yl]methyl]heptan-4-ol, Oct. 26, 2006, 10 pages.
Ali, A., et al., Synthesis and Face- and Stereo-selective Cycloadditions of α-Alkoxy Cyclic Nitrones, Tetrahedron Letters, 1998, vol. 29, pp. 1255-1256.
Tamura, O., et al., Chelation Controlled 1,3-Dipolar Cycloaddition of 5,6-Dihydro-5-phenyl-I,4-oxazin-2-one N-Oxide with Allyl Alcohols: A Short-step Synthesis of Clavalanine Intermediate, Tetrahedron Letters, 1999, vol. 40. pp. 895-898.
Pubchem CID 10955779, (2S)-1-[(3S)-Morpholin-3-yl]-4-propylheptan-2-ol, Oct. 26, 2006, 10 pages.
Hudson, A., et al., Electron Spin Resonance of Aliphatic Nitroxides. Part II. The Cyclic Radicals from Pyrrolidine, Piperidine, Morpholine, and Hexamethyleneimine, Journal of the Chemical Society B: Physical Organic, 1968, pp. 251-253.
Cordero, F.M., et al., The Synthesis of 4-Hydroxypipecolic Acids by Stereoselective Cycloaddition of Configurationally Stable Nitrones, European Journal of Organic Chemistry, 2006, pp. 3235-3241.
Machetti, F., et al., Synthesis of Free and Nα-Fmoc-/Nγ-Boc-Protected (2S,4S)- and (2S,4R)-4-Aminopipecolic Acids, European Journal of Organic Chemistry, Jun. 15, 2004, vol. 2004, No. 13, pp. 2928-2935.
Gothelf, K.V., et al., A Highly Diastereoselective and Enantioselective Ti(OTos)2-TADDOLate-Catalyzed 1,3-Dipolar Cycloaddition Reaction of Alkenes with Nitrones, Journal of the American Chemical Society, Jan. 10, 1996, vol. 118, No. 1, pp. 59-64.

* cited by examiner

*Primary Examiner* — D Margaret M Seaman
(74) *Attorney, Agent, or Firm* — Hodgson Russ LLP

(57) ABSTRACT

Disclosed are methods of making delmopinol and delmopinol salts (e.g., delmopinol metal salts, such as, for example, delmopinol calcium salts, delmopinol sodium salts, delmopinol potassium salts, and/or delmopinol magnesium salts). Delmopinol has structure (I) and a salt of delmopinol has structure

20 Claims, 25 Drawing Sheets

| | B | C | D | E |
|---|---|---|---|---|
| 4 | | Chemical Purity of Delmopinol and Estimation of Related Impurities | | |
| 5 | | Lab NoteBook Reference: IN-KNP-C-204 Date: JUL 17, 2018 | | |
| 6 | Sample | Area | 100% Corrected Area | |
| 7 | 1% Solution; Lot# IN-KVK-D-144-1 Prep-1 Corrected area | 36 | 3565 | |
| 8 | Lot# | | IN-KVK-D-144-1 Prep-1 | |
| 9 | | RT | Area | Area % |
| 10 | | 17.40 | 11 | 0.31 |
| 11 | | 18.63 | 5 | 0.13 |
| 12 | | 19.49 | 4 | 0.12 |
| 13 | | 19.79 | 4 | 0.10 |
| 14 | | 20.12 | 8 | 0.22 |
| 15 | | 21.27 | 3 | 0.09 |
| 16 | | 21.50 | 6 | 0.16 |
| 17 | | 22.98 | 1 | 0.03 |
| 18 | 1% Sample corrected for 100% | 23.66 | 3565 | 96.24 |
| 19 | | 24.01 | 2 | 0.06 |
| 20 | | 24.31 | 26 | 0.69 |
| 21 | | 24.81 | 26 | 0.71 |
| 22 | | 25.01 | 6 | 0.16 |
| 23 | | 26.17 | 5 | 0.14 |
| 24 | | 27.18 | 19 | 0.51 |
| 25 | | 29.60 | 4 | 0.11 |
| 26 | | 29.81 | 9 | 0.23 |
| 27 | Total Area | | 3704 | 100 |
| 28 | | | | |
| 29 | | | | |
| 30 | | Chemical Purity of Delmopinol and Estimation of Related Impurities | | |
| 31 | | Lab NoteBook Reference: IN-KNP-C-204 Date: JUL 17, 2018 | | |
| 32 | Sample | Area | 100% Corrected Area | |
| 33 | 1% Solution; Lot# IN-KVK-D-144-1 Prep-2 Corrected area | 36 | 3589 | |
| 34 | Lot# | | IN-KVK-D-144-1 Prep-2 | |
| 35 | | RT | Area | Area % |
| 36 | | 17.40 | 13 | 0.35 |
| 37 | | 18.62 | 3 | 0.09 |
| 38 | | 19.49 | 6 | 0.15 |
| 39 | | 19.79 | 3 | 0.09 |
| 40 | | 20.10 | 10 | 0.26 |
| 41 | | 21.26 | 5 | 0.12 |
| 42 | | 21.54 | 4 | 0.09 |
| 43 | | 22.98 | 1 | 0.03 |
| 44 | 1% Sample corrected for 100% | 23.65 | 3589 | 96.02 |
| 45 | | 23.99 | 3 | 0.09 |
| 46 | | 24.31 | 27 | 0.72 |
| 47 | | 24.81 | 25 | 0.67 |
| 48 | | 25.38 | 11 | 0.30 |
| 49 | | 26.18 | 6 | 0.16 |
| 50 | | 27.17 | 20 | 0.54 |
| 51 | | 29.47 | 3 | 0.08 |
| 52 | | 29.87 | 9 | 0.24 |
| 53 | Total Area | | 3738 | 100 |

Figure 6

| | B | C | D | E |
|---|---|---|---|---|
| 4 | Chemical Purity of Delmopinol and Estimation of Related Impurities | | | |
| 5 | Lab NoteBook Reference: IN-KNP-C-204  Date: JUL 17, 2018 | | | |
| 6 | Sample | Area | 100% Corrected Area | |
| 7 | 1% Solution; Lot# IN-KVK-D-144-1 Prep-1 Corrected area | 35.65 | =C7*100 | |
| 8 | Lot# | | IN-KVK-D-144-1 Prep-1 | |
| 9 | | RT | Area | Area % |
| 10 | | 17.4 | 11.46 | =D10/$D$27*100 |
| 11 | | 18.63 | 4.72 | =D11/$D$27*100 |
| 12 | | 19.49 | 4.43 | =D12/$D$27*100 |
| 13 | | 19.79 | 3.55 | =D13/$D$27*100 |
| 14 | | 20.12 | 8.02 | =D14/$D$27*100 |
| 15 | | 21.27 | 3.47 | =D15/$D$27*100 |
| 16 | | 21.5 | 5.88 | =D16/$D$27*100 |
| 17 | | 22.98 | 1.16 | =D17/$D$27*100 |
| 18 | 1% Sample corrected for 100% | 23.66 | =D7 | =D18/$D$27*100 |
| 19 | | 24.01 | 2.06 | =D19/$D$27*100 |
| 20 | | 24.31 | 25.08 | =D20/$D$27*100 |
| 21 | | 24.81 | 26.44 | =D21/$D$27*100 |
| 22 | | 25.01 | 5.83 | =D22/$D$27*100 |
| 23 | | 26.17 | 5.11 | =D23/$D$27*100 |
| 24 | | 27.18 | 19.04 | =D24/$D$27*100 |
| 25 | | 29.6 | 3.9 | =D25/$D$27*100 |
| 26 | | 29.81 | 8.51 | =D26/$D$27*100 |
| 27 | Total Area | | =SUM(D10:D26) | =SUM(E10:E26) |
| 28 | | | | |
| 29 | | | | |
| 30 | Chemical Purity of Delmopinol and Estimation of Related Impurities | | | |
| 31 | Lab NoteBook Reference: IN-KNP-C-204  Date: JUL 17, 2018 | | | |
| 32 | Sample | Area | 100% Corrected Area | |
| 33 | 1% Solution; Lot# IN-KVK-D-144-1 Prep-2 Corrected area | 35.80 | =C33*100 | |
| 34 | Lot# | | IN-KVK-D-144-1 Prep-2 | |
| 35 | | RT | Area | Area % |
| 36 | | 17.4 | 13.11 | =D36/$D$53*100 |
| 37 | | 18.62 | 3.26 | =D37/$D$53*100 |
| 38 | | 19.49 | 5.72 | =D38/$D$53*100 |
| 39 | | 19.79 | 3.22 | =D39/$D$53*100 |
| 40 | | 20.1 | 9.66 | =D40/$D$53*100 |
| 41 | | 21.26 | 4.52 | =D41/$D$53*100 |
| 42 | | 21.54 | 3.55 | =D42/$D$53*100 |
| 43 | | 22.98 | 1.14 | =D43/$D$53*100 |
| 44 | 1% Sample corrected for 100% | 23.65 | =D33 | =D44/$D$53*100 |
| 45 | | 23.99 | 3.47 | =D45/$D$53*100 |
| 46 | | 24.31 | 26.93 | =D46/$D$53*100 |
| 47 | | 24.81 | 25.02 | =D47/$D$53*100 |
| 48 | | 25.38 | 11.37 | =D48/$D$53*100 |
| 49 | | 26.18 | 5.86 | =D49/$D$53*100 |
| 50 | | 27.17 | 20.04 | =D50/$D$53*100 |
| 51 | | 29.47 | 2.96 | =D51/$D$53*100 |
| 52 | | 29.87 | 8.9 | =D52/$D$53*100 |
| 53 | Total Area | | =SUM(D36:D52) | =SUM(E36:E52) |

Figure 7

```
Column used : Sunfire C18 150 * 4.6mm ,3.5um
Mobile Phase A : 25mM Ammonium acetate
Mobile Phase B :Methanol:Acetonitrile (50:50 %v/v)
Detector : CAD    Flow rate :1ml/ min    Column Temperature:25°c
Diluent : Methanol (100%)
Gradient : Time / %B :0/30 5/30 20/80 30/80 30.1/30 35/30
```

```
CAD1 A, CAD Signal A
#   Compound Name    Ret. Time    Area      Area %
----------------------------------------------------
1   Delmopinol         23.60      35.65     100.00
```

Column used : Sunfire C18 150 * 4.6mm, 3.5um
Mobile Phase A : 25mM Ammonium acetate
Mobile Phase B : Methanol:Acetonitrile (50:50 %v/v)
Detector : CAD    Flow rate : 1ml/min    Column Temperature: 25°c
Diluent : Methanol (100%)
Gradient : Time / %B : 0/30  5/30  20/80  30/80  30.1/30  35/30

CAD1 A, CAD Signal A

| # | Compound Name | Ret. Time | Area | Area % |
|---|---|---|---|---|
| 1 |  | 17.40 | 11.46 | 0.46 |
| 2 |  | 18.63 | 4.72 | 0.19 |
| 3 |  | 19.49 | 4.43 | 0.18 |
| 4 |  | 19.79 | 3.55 | 0.14 |
| 5 |  | 20.12 | 8.02 | 0.32 |
| 6 |  | 21.27 | 3.47 | 0.14 |
| 7 |  | 21.50 | 5.88 | 0.24 |
| 8 |  | 22.98 | 1.16 | 0.05 |
| 9 | Delmopinol | 23.66 | 2362.85 | 94.43 |
| 10 |  | 24.01 | 2.06 | 0.08 |

PPL_LCMS_002_CAD    Tue, 17. Jul. 2018    00:29:38 pm    Page 1 of 2

| # | Compound Name | Ret. Time | Area | Area % |
|---|---|---|---|---|
| 11 | | 24.31 | 25.68 | 1.03 |
| 12 | | 24.81 | 26.44 | 1.06 |
| 13 | | 25.01 | 5.83 | 0.23 |
| 14 | | 26.17 | 5.11 | 0.20 |
| 15 | | 27.18 | 19.04 | 0.76 |
| 16 | | 29.60 | 3.90 | 0.16 |
| 17 | | 29.81 | 8.51 | 0.34 |

Figure 9 (cont.)

| # | Compound Name | Ret. Time | Area | Area % |
|---|---|---|---|---|
| 11 | | 24.31 | 26.93 | 1.07 |
| 12 | | 24.81 | 25.02 | 0.99 |
| 13 | | 25.38 | 11.37 | 0.45 |
| 14 | | 26.18 | 5.86 | 0.25 |
| 15 | | 27.17 | 20.04 | 0.79 |
| 16 | | 29.47 | 2.96 | 0.12 |
| 17 | | 29.87 | 8.90 | 0.35 |

Figure 11 (cont.)

|   | B | C | D | E |
|---|---|---|---|---|
| 4 | Chemical Purity of Delmopinol and Estimation of Related Impurities | | | |
| 5 | Lab NoteBook Reference: IN-KNP-D-21 Date: AUG 06, 2018 | | | |
| 6 | Sample | Area | 100% Corrected Area | |
| 7 | 1% Solution; Lot# IN-KVK-D-168-1 | 59.49 | | |
| 8 | Blank Interference | 9.83 | | |
| 9 | 1% Solution; Lot# IN-KVK-D-168-1 Corrected area | 49.66 | 4966 | |
| 10 | Lot# | IN-KVK-D-168-1 Prep-1 | | |
| 11 | | RT | Area | Area % |
| 12 | | 17.31 | 7.12 | 0.14 |
| 13 | | 19.43 | 10.10 | 0.20 |
| 14 | | 21.47 | 8.76 | 0.17 |
| 15 | | 22.97 | 2.27 | 0.04 |
| 16 | 1% Sample corrected for 100% | 23.62 | 4966.00 | 97.26 |
| 17 | | 23.87 | 11.45 | 0.22 |
| 18 | | 24.26 | 38.57 | 0.76 |
| 19 | | 24.75 | 37.55 | 0.74 |
| 20 | | 24.98 | 12.96 | 0.25 |
| 21 | | 26.00 | 3.98 | 0.08 |
| 22 | | 27.08 | 7.33 | 0.14 |
| 23 | Total Area | | 5106 | 100 |
| 24 | | | | |
| 25 | | | | |
| 26 | Chemical Purity of Delmopinol and Estimation of Related Impurities | | | |
| 27 | Lab NoteBook Reference: IN-KNP-D-21 Date: AUG 06, 2018 | | | |
| 28 | Sample | Area | 100% Corrected Area | |
| 29 | 1% Solution; Lot# IN-KVK-D-168-1 | 68.35 | | |
| 30 | Blank Interference | 9.83 | | |
| 31 | 1% Solution; Lot# IN-KVK-D-168-1 Corrected area | 58.52 | 5852 | |
| 32 | Lot# | IN-KVK-D-168-1 Prep-2 | | |
| 33 | | RT | Area | Area % |
| 34 | | 17.30 | 9.87 | 0.16 |
| 35 | | 19.42 | 15.19 | 0.25 |
| 36 | | 21.46 | 18.58 | 0.31 |
| 37 | | 22.92 | 6.31 | 0.10 |
| 38 | 1% Sample corrected for 100% | 23.59 | 5852.00 | 96.45 |
| 39 | | 23.90 | 9.16 | 0.15 |
| 40 | | 24.23 | 62.09 | 1.02 |
| 41 | | 24.73 | 59.82 | 0.99 |
| 42 | | 24.99 | 9.36 | 0.15 |
| 43 | | 26.10 | 5.95 | 0.10 |
| 44 | | 26.95 | 4.13 | 0.07 |
| 45 | | 27.04 | 14.79 | 0.24 |
| 46 | Total Area | | 6067 | 100 |

Figure 15

|   | B | C | D | E |
|---|---|---|---|---|
| 4 | Chemical Purity of Delmopinol and Estimation of Related Impurities | | | |
| 5 | Lab NoteBook Reference: IN-KNP-D-21 Date: AUG 06, 2018 | | | |
| 6 | Sample | Area | 100% Corrected Area | |
| 7 | 1% Solution; Lot# IN-KVK-D-168-1 | 59.49 | | |
| 8 | Blank Interference | 9.83 | | |
| 9 | 1% Solution; Lot# IN-KVK-D-168-1 Corrected area | =C7-C8 | =C9*100 | |
| 10 | Lot# | | IN-KVK-D-168-1 Prep-1 | |
| 11 | | RT | Area | Area % |
| 12 | | 17.31 | 7.12 | =D12/$D$23*100 |
| 13 | | 19.43 | 10.1 | =D13/$D$23*100 |
| 14 | | 21.47 | 8.76 | =D14/$D$23*100 |
| 15 | | 22.97 | 2.27 | =D15/$D$23*100 |
| 16 | 1% Sample corrected for 100% | 23.62 | =D9 | =D16/$D$23*100 |
| 17 | | 23.87 | 11.45 | =D17/$D$23*100 |
| 18 | | 24.26 | 38.57 | =D18/$D$23*100 |
| 19 | | 24.75 | 37.55 | =D19/$D$23*100 |
| 20 | | 24.98 | 12.96 | =D20/$D$23*100 |
| 21 | | 26 | 3.98 | =D21/$D$23*100 |
| 22 | | 27.08 | 7.33 | =D22/$D$23*100 |
| 23 | Total Area | | =SUM(D12:D22) | =SUM(E12:E22) |
| 24 | | | | |
| 25 | | | | |
| 26 | Chemical Purity of Delmopinol and Estimation of Related Impurities | | | |
| 27 | Lab NoteBook Reference: IN-KNP-D-21 Date: AUG 06, 2018 | | | |
| 28 | Sample | Area | 100% Corrected Area | |
| 29 | 1% Solution; Lot# IN-KVK-D-168-1 | 68.35 | | |
| 30 | Blank Interference | 9.83 | | |
| 31 | 1% Solution; Lot# IN-KVK-D-168-1 Corrected area | =C29-C30 | =C31*100 | |
| 32 | Lot# | | IN-KVK-D-168-1 Prep-2 | |
| 33 | | RT | Area | Area % |
| 34 | | 17.3 | 9.87 | =D34/$D$46*100 |
| 35 | | 19.42 | 15.19 | =D35/$D$46*100 |
| 36 | | 21.46 | 18.58 | =D36/$D$46*100 |
| 37 | | 22.92 | 6.31 | =D37/$D$46*100 |
| 38 | 1% Sample corrected for 100% | 23.59 | =D31 | =D38/$D$46*100 |
| 39 | | 23.9 | 9.16 | =D39/$D$46*100 |
| 40 | | 24.23 | 62.09 | =D40/$D$46*100 |
| 41 | | 24.73 | 59.82 | =D41/$D$46*100 |
| 42 | | 24.99 | 9.36 | =D42/$D$46*100 |
| 43 | | 26.1 | 5.95 | =D43/$D$46*100 |
| 44 | | 26.95 | 4.13 | =D44/$D$46*100 |
| 45 | | 27.04 | 14.79 | =D45/$D$46*100 |
| 46 | Total Area | | =SUM(D34:D45) | =SUM(E34:E45) |
| 47 | | | | |

Figure 16

Column used : Sunfire C18 150 * 4.6mm ,3.5um
Mobile Phase A : 25mM Ammonium acetate
Mobile Phase B : Methanol:Acetonitrile (50:50 %v/v)
Detector : CAD    Flow rate : 1ml/ min    Column Temperature:25°c
Diluent : Water:Acetonitrile (50:50% v/v)
Gradient : Time / %B : 0/30 5/30 20/80 30/80 30.1/30 35/30

CAD1 A, CAD Signal A

| # | Ret. Time | Area | Area % |
|---|---|---|---|
| 1 | 17.31 | 7.12 | 0.51 |
| 2 | 19.43 | 10.10 | 0.72 |
| 3 | 21.47 | 8.76 | 0.62 |
| 4 | 22.97 | 2.27 | 0.16 |
| 5 | 23.62 | 1263.74 | 90.02 |
| 6 | 23.87 | 11.45 | 0.82 |
| 7 | 24.26 | 38.57 | 2.75 |
| 8 | 24.75 | 37.55 | 2.67 |
| 9 | 24.98 | 12.96 | 0.92 |
| 10 | 26.00 | 3.98 | 0.28 |

```
Column used : Sunfire C18 150 * 4.6mm ,3.5um
Mobile Phase A : 25mM Ammonium acetate
Mobile Phase B :Methanol:Acetonitrile (50:50 %v/v)
Detector : CAD    Flow rate :1ml/ min    Column Temperature:25°c
Diluent : Water:Acetonitrile (50:50% v/v)
Gradient : Time / %B :0/30 5/30 20/80 30/80 30.1/30 35/30
```

```
CAD1 A, CAD Signal A
 #      Ret. Time       Area         Area %
 1       17.30           9.87         0.38
 2       19.42          15.19         0.59
 3       21.46          18.58         0.72
 4       22.92           6.31         0.25
 5       23.59        2356.87        91.63
 6       23.90           9.16         0.36
 7       24.23          62.09         2.41
 8       24.73          59.82         2.33
 9       24.99           9.36         0.36
10       26.10           5.95         0.23
```

| # | Ret. Time | Area | Area % |
|---|---|---|---|
| 11 | 26.95 | 4.13 | 0.16 |
| 12 | 27.04 | 14.79 | 0.57 |

Figure 21 (cont.)

METHODS OF MAKING DELMOPINOL AND SALTS THEREOF

CROSS REFERENCE TO RELATED APPLICATIONS

This application claims priority to U.S. Provisional Application No. 62/968,730, filed Jan. 31, 2020, the disclosure of which is incorporated herein by reference.

BACKGROUND OF THE DISCLOSURE

Delmopinol is an anti-plaque agent often used in mouthwashes and oral rinses. Delmopinol has also been shown to have a low antimicrobial effect in vitro. Of interest are synthetic methods with fewer synthetic steps to produce delmopinol than methods commercially used.

SUMMARY OF THE DISCLOSURE

The present disclosure provides methods of making delmopinol and delmopinol salts (e.g., delmopinol metal salts, such as, for example, delmopinol calcium salts, delmopinol sodium salts, delmopinol potassium salts, and/or delmopinol magnesium salts).

In an aspect, the present disclosure provides methods of making delmopinol and delmopinol salts (e.g., delmopinol calcium salts, delmopinol sodium salts, delmopinol potassium salts, and/or delmopinol magnesium salts). A method of making delmopinol and delmopinol salts (e.g., delmopinol calcium salts, delmopinol sodium salts, delmopinol potassium salts, and/or delmopinol magnesium salts) may comprise:

contacting

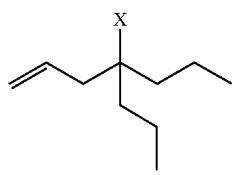

with a first reaction mixture comprising: morpholine, a first solvent, $H_2O_2$, and $Na_2WO_4 \cdot 2H_2O$, where

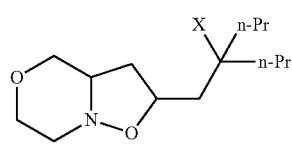

is formed (e.g., reacting

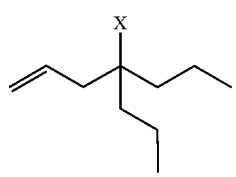

with morpholine, $H_2O_2$ and $Na_2WO_4 \cdot 2H_2O$ in a solvent) and X is an alcohol, an —O⁻, or a protected alcohol (e.g., OTs or the like) contacting

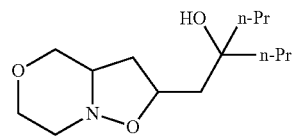

with a second reaction mixture comprising: p-toluenesulfonic acid, a second solvent, $H_2$ gas at a pressure of at least 10 kg/cm², and Pd/C, where

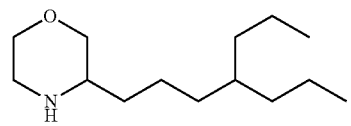 [SMILES: CCCC(CCC)CCCC1COCCN1]

is formed (e.g., reacting

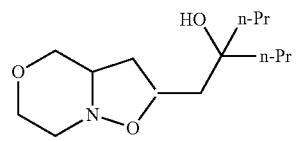

with p-toluenesulfonic acid under hydrogenation conditions (e.g., under a hydrogen pressure with 10% Pd/C) in a solvent); contacting

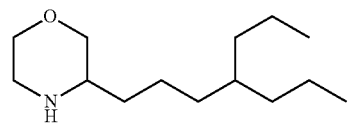 [SMILES: CCCC(CCC)CCCC1COCCN1]

with a third reaction mixture comprising: a third solvent, a salt (e.g., KI, NI, tetrabutylammonium iodide (TBAI), tetrabutylammonium bromide (TBAB), and the like), a base (which is optional), and a halogenated ethyl alcohol (e.g., 2-chloroethanol, 2-bromoethanol), ethylene oxide, or a halogenated ethane comprising a protected alcohol (e.g., OTs or the like) where

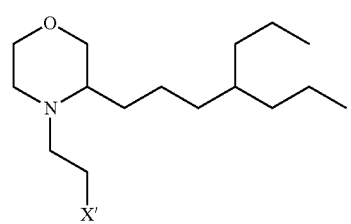

is formed (e.g., reacting

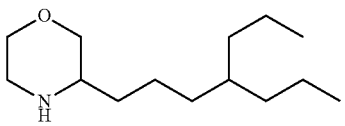 [SMILES: CCCC(CCC)CCCC1COCCN1]

with a salt (e.g., a nucleophilic catalyst, such as, for example KI), a base (e.g., KOH), a halogenated ethyl alcohol (e.g., 2-chloroethanol), a halogenated ethane having a protected alcohol, or ethylene oxide) and X' is an alcohol or a protected alcohol (e.g., OTs or the like); and contacting

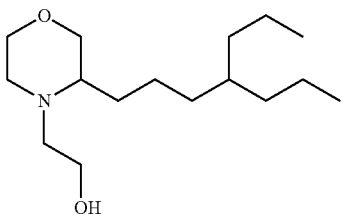 [SMILES: CCCC(CCC)CCCC1COCCN1CCO]

with a metal salt, where

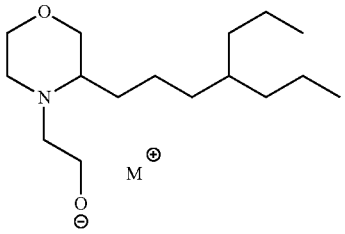

is formed (e.g., reacting

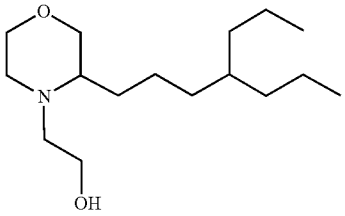 [SMILES: CCCC(CCC)CCCC1COCCN1CCO]

with a metal salt in a solvent (e.g., ethanol)) and $M^+$ is a metal cation, with the proviso that the method does not comprise formation of

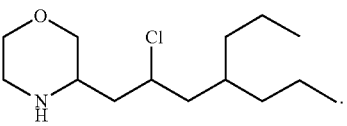 [SMILES: CCCC(CCC)CC(Cl)CC1COCCN1]

BRIEF DESCRIPTION OF THE FIGURES

For a fuller understanding of the nature and objects of the disclosure, reference should be made to the following detailed description taken in conjunction with the accompanying figures.

FIG. 6 shows a table of the chemical purity of delmopinol and estimation of the related impurities.

FIG. 7 shows a table of the chemical purity of delmopinol and estimation of the related impurities.

FIG. 15 shows a table of the chemical purity of delmopinol and estimation of the related impurities.

FIG. 16 shows a table of the chemical purity of delmopinol and estimation of the related impurities.

DETAILED DESCRIPTION OF THE DISCLOSURE

Figure 1:
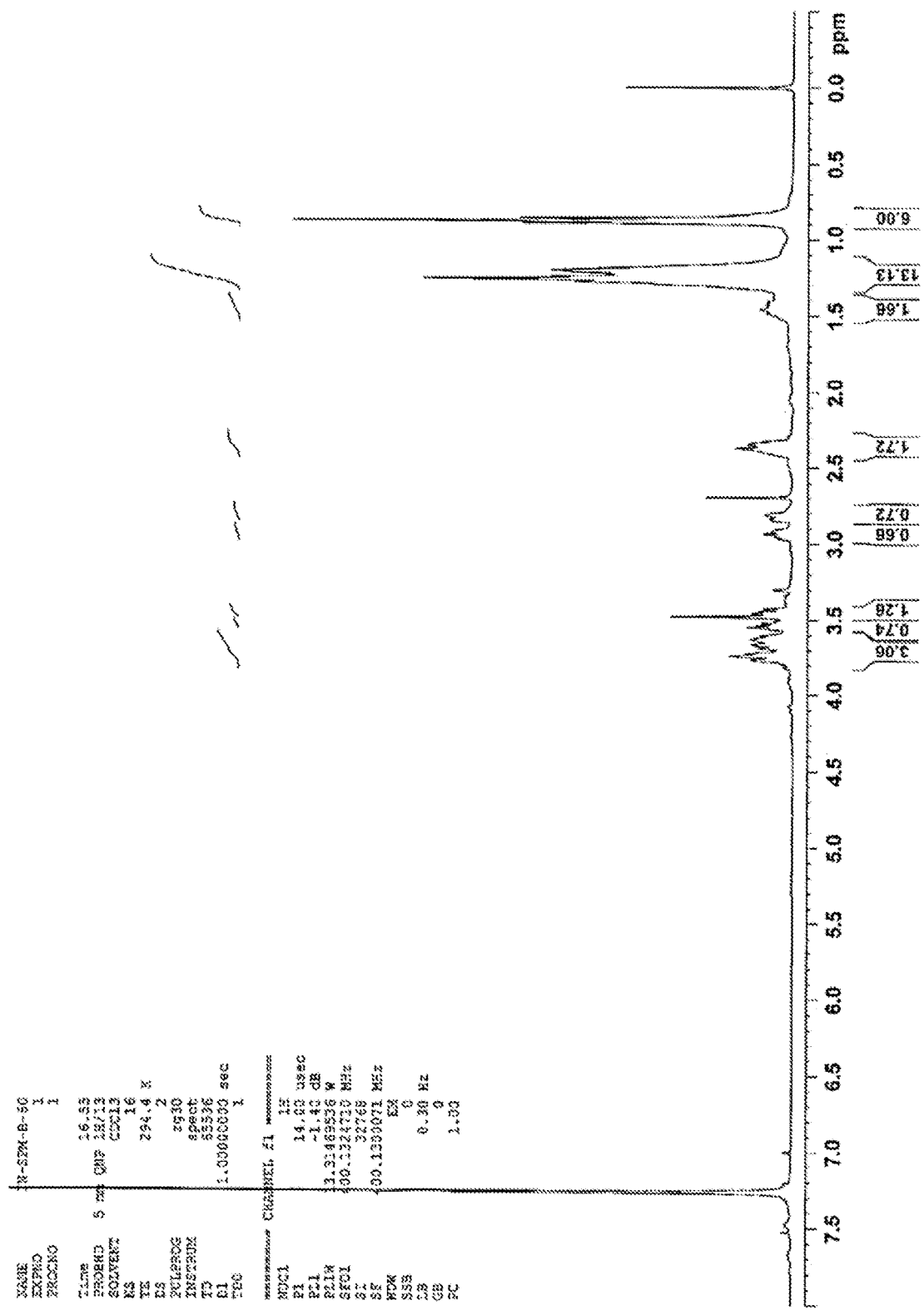
FIG. 1 shows an $^1$H NMR spectrum of delmopinol sodium salt.
Figure 2:
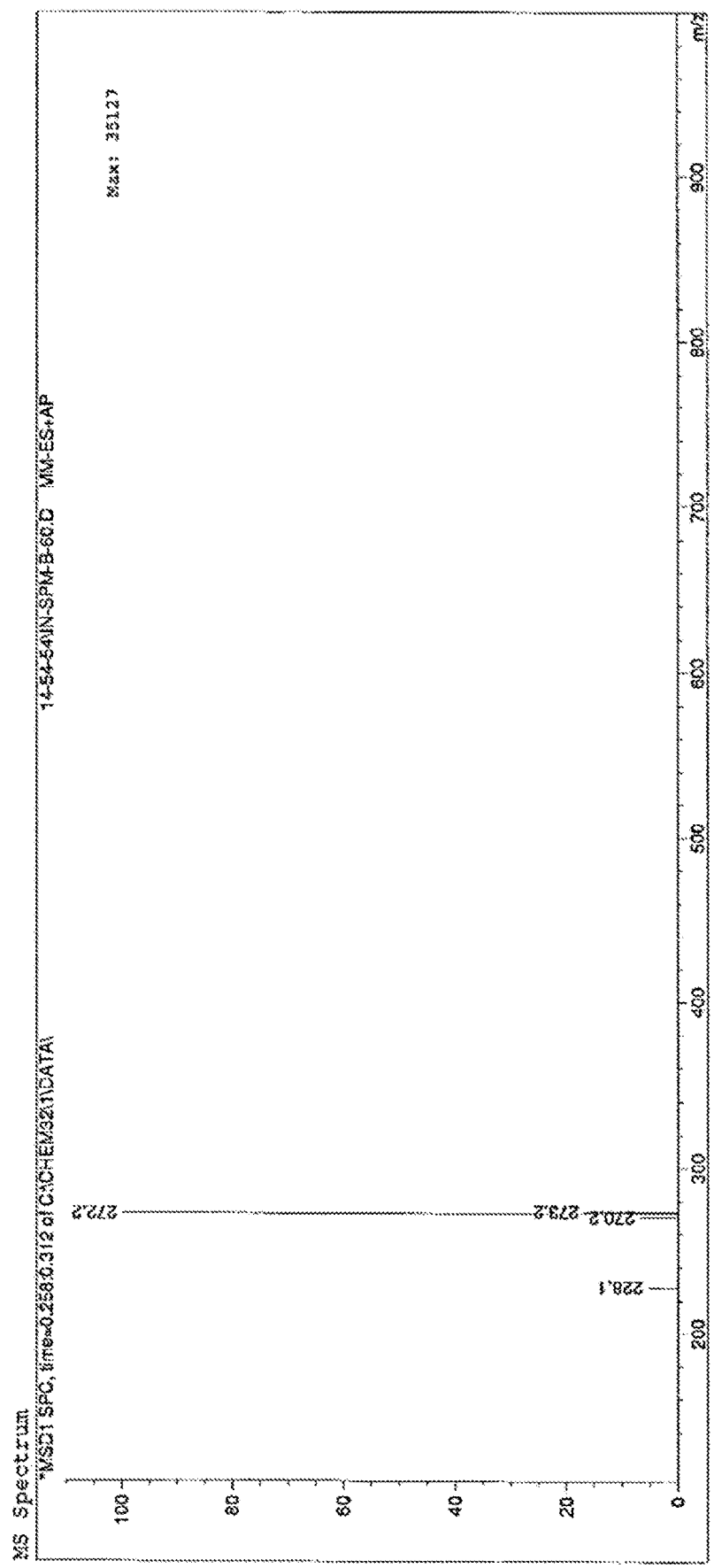
FIG. 2 shows a mass spectrum of delmopinol sodium salt.
Figure 3:
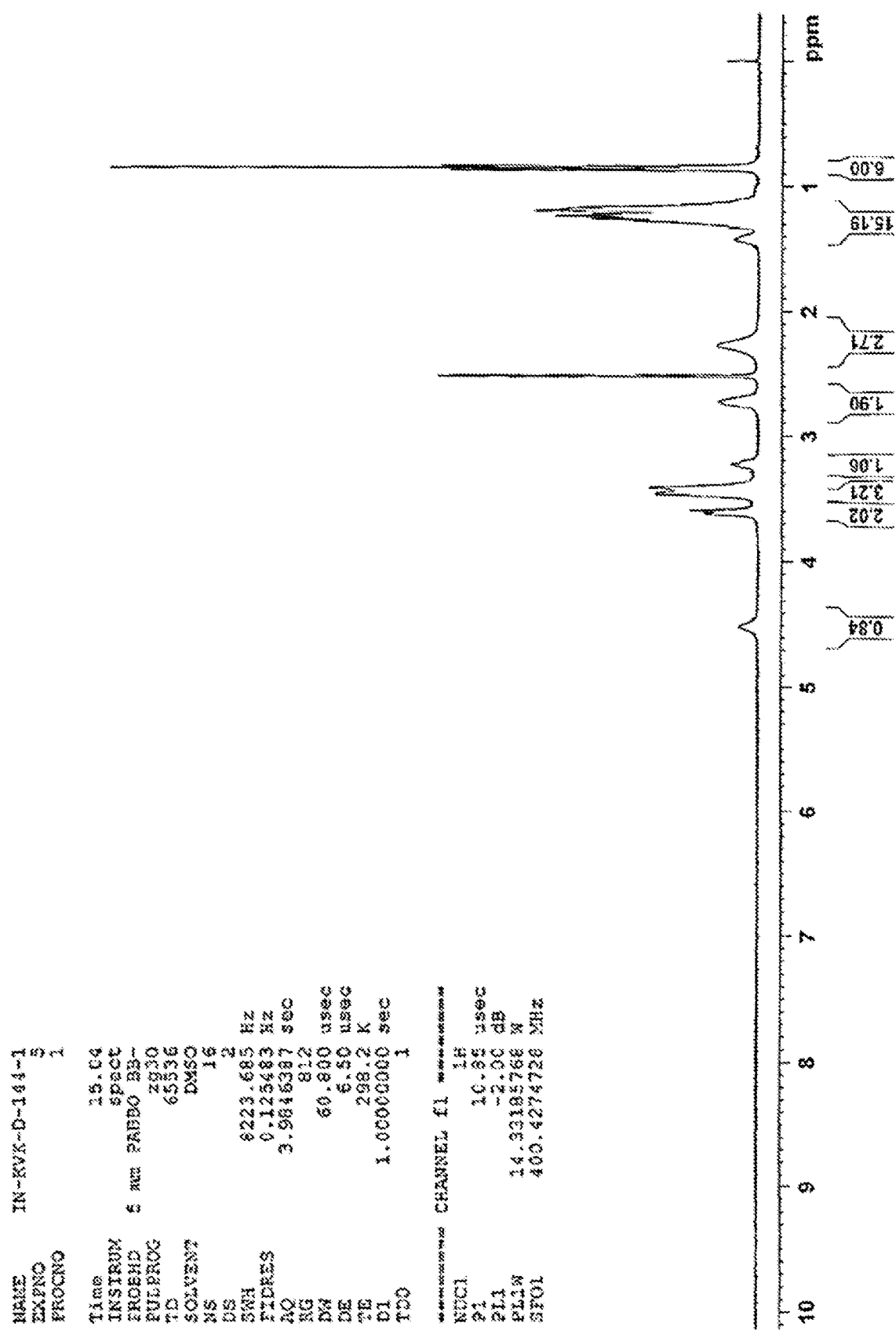
FIG. 3 shows an $^1$H NMR spectrum of delmopinol calcium salt.
Figure 4:
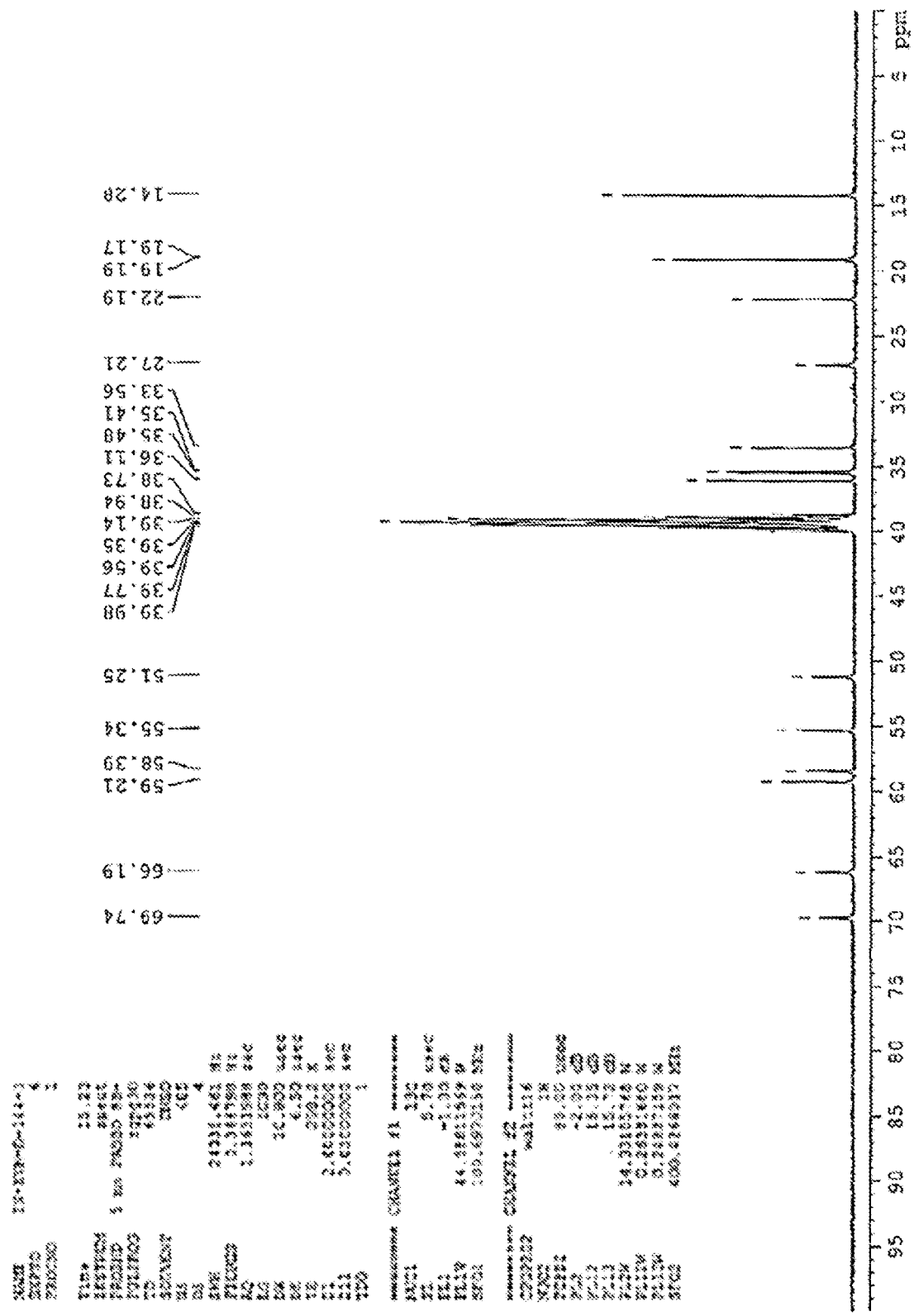
FIG. 4 shows a $^{13}$C NMR spectrum of delmopinol calcium salt.
Figure 5:
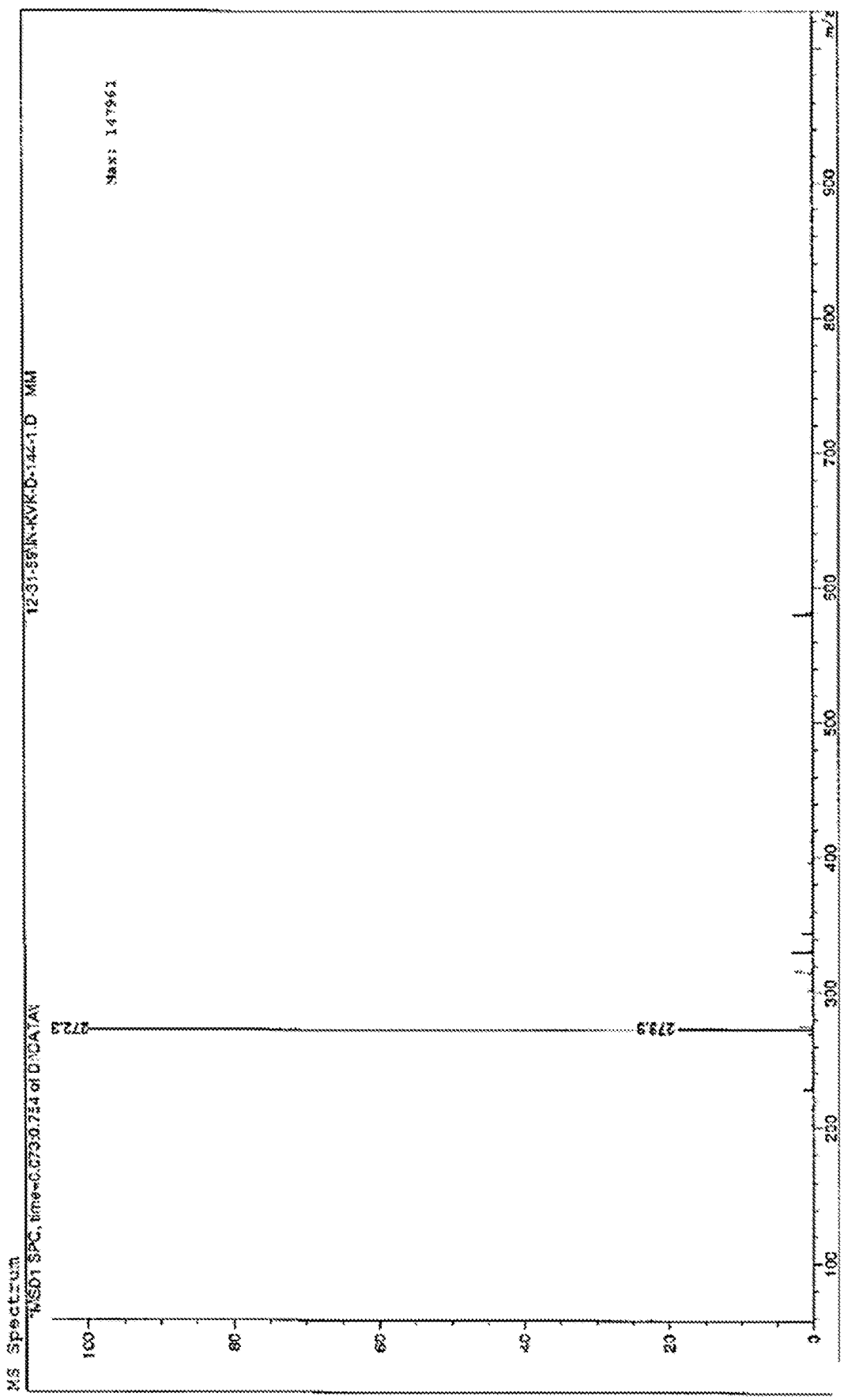
FIG. 5 shows a mass spectrum of delmopinol calcium salt.
Figure 8:
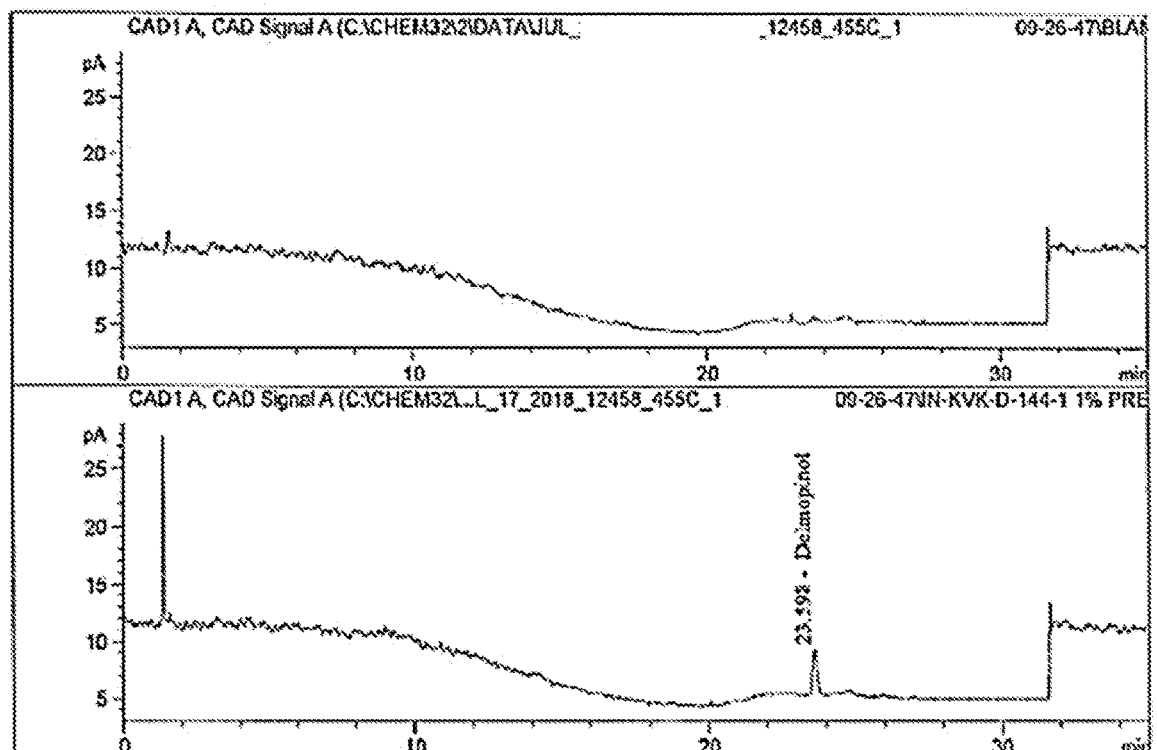
FIG. 8 shows an HPLC chromatogram of delmopinol salt. The detector used was a charged aerosol detector (CAD).
Figure 9:
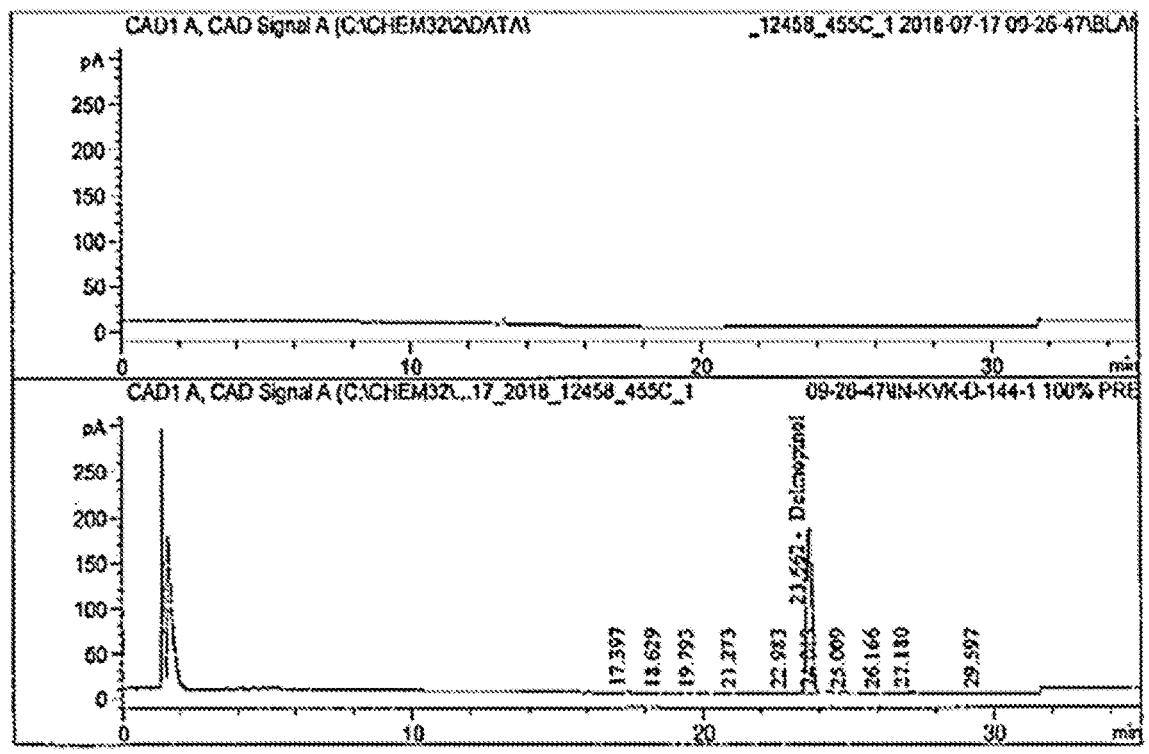
FIG. 9 shows an HPLC chromatogram of delmopinol salt. The detector used was a CAD.
Figure 10:
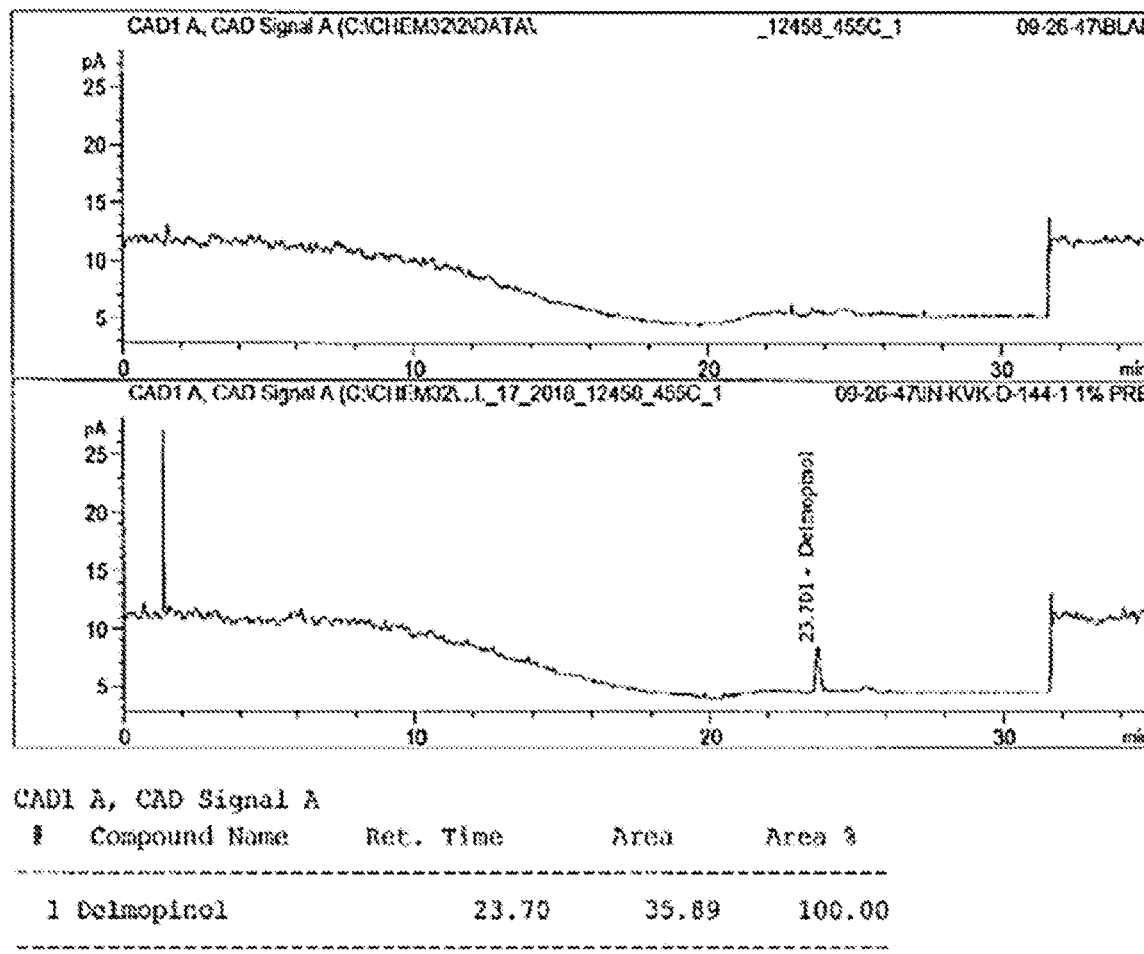
FIG. 10 shows an HPLC chromatogram of delmopinol salt. The detector used was a CAD.
Figure 11:
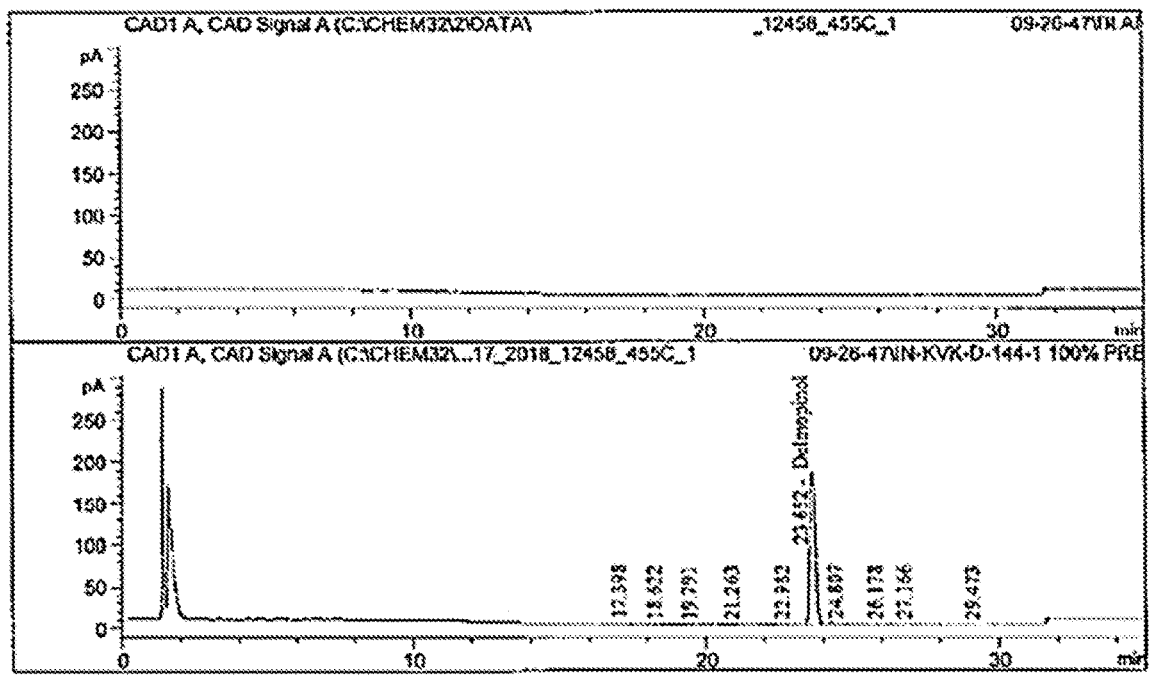
FIG. 11 shows an HPLC chromatogram of delmopinol salt. The detector used was a CAD.
Figure 12:
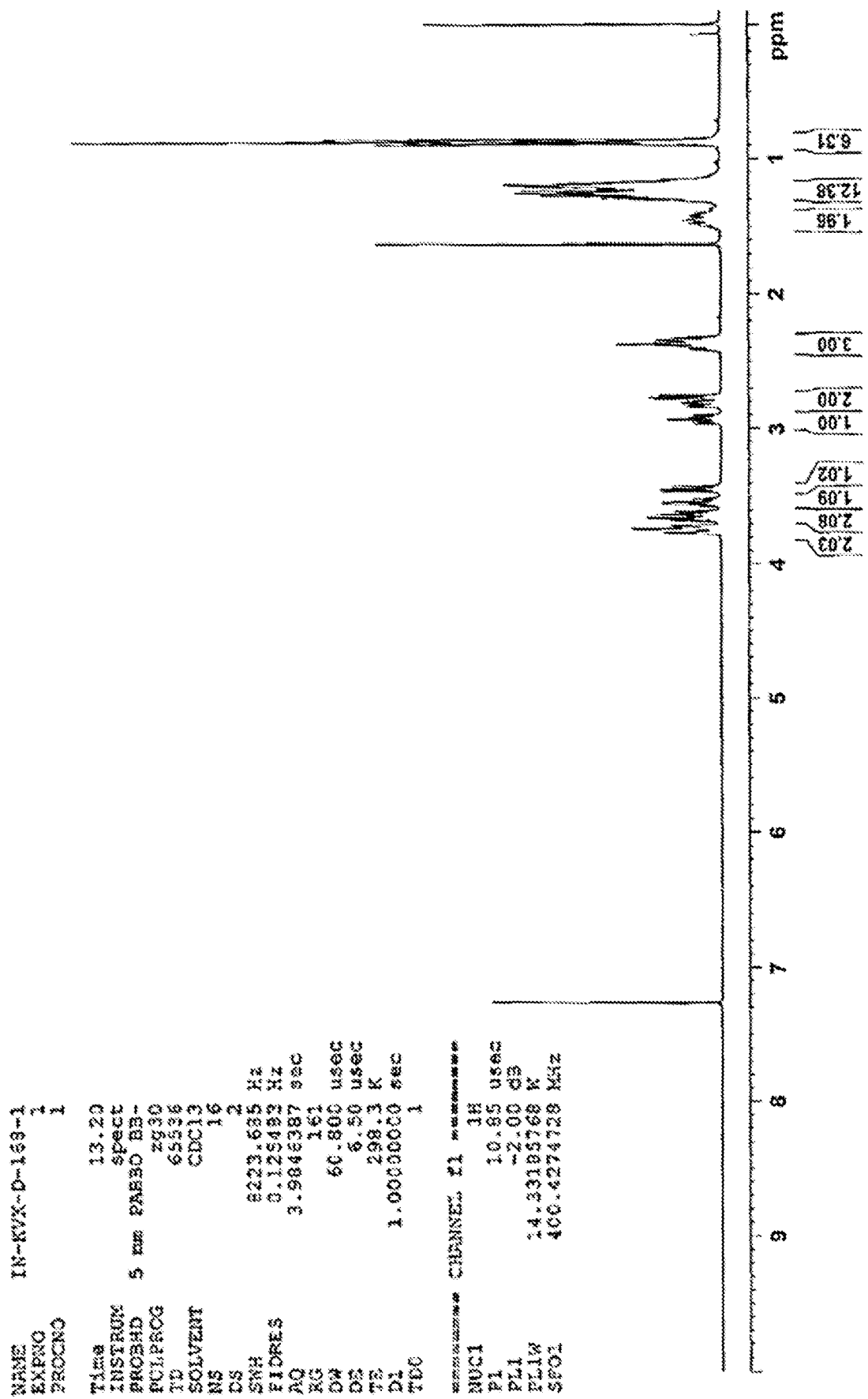
FIG. 12 shows an $^1$H NMR spectrum of delmopinol sodium salt.
Figure 13:
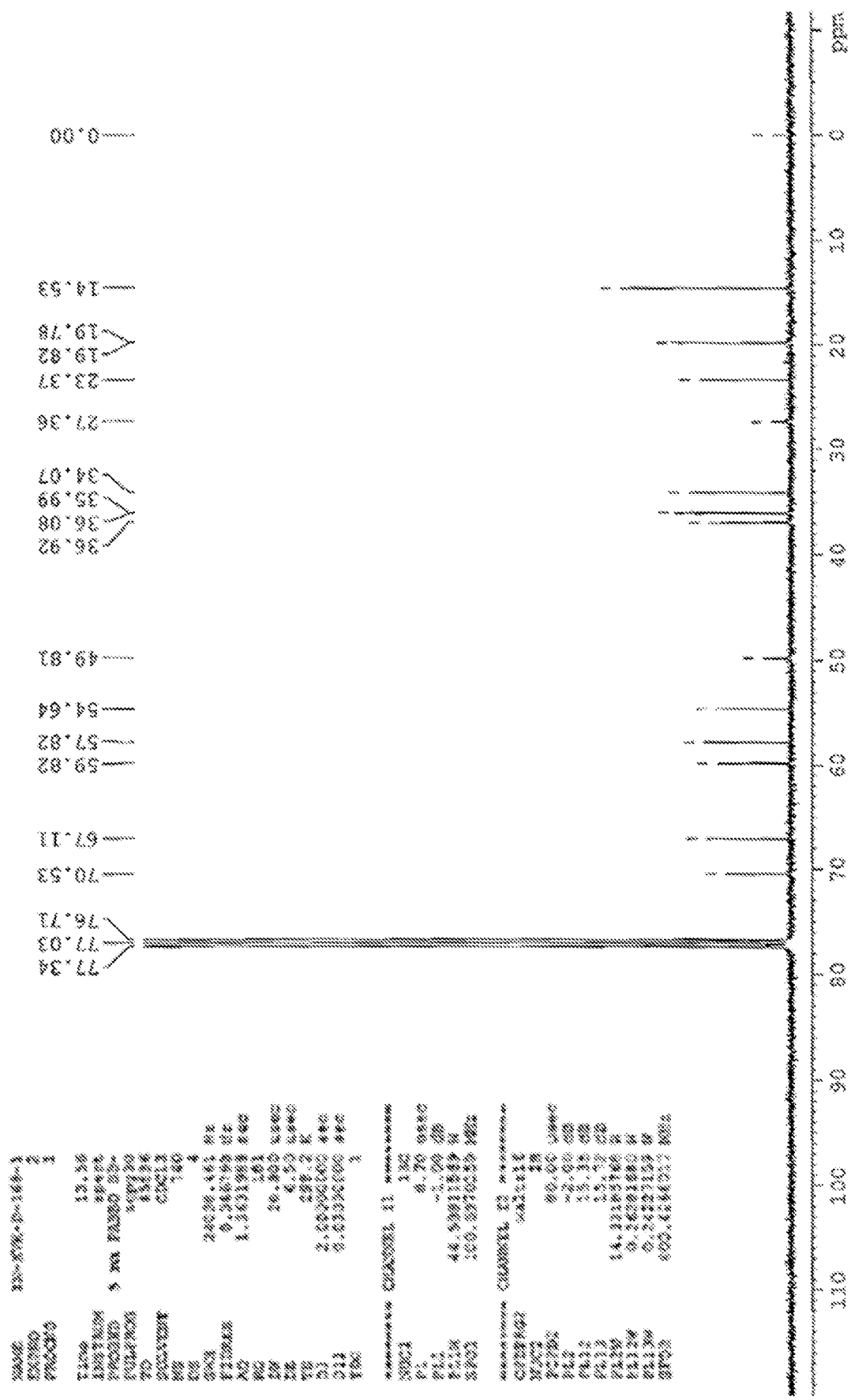
FIG. 13 shows a $^{13}$C NMR spectrum of delmopinol sodium salt.
Figure 14:
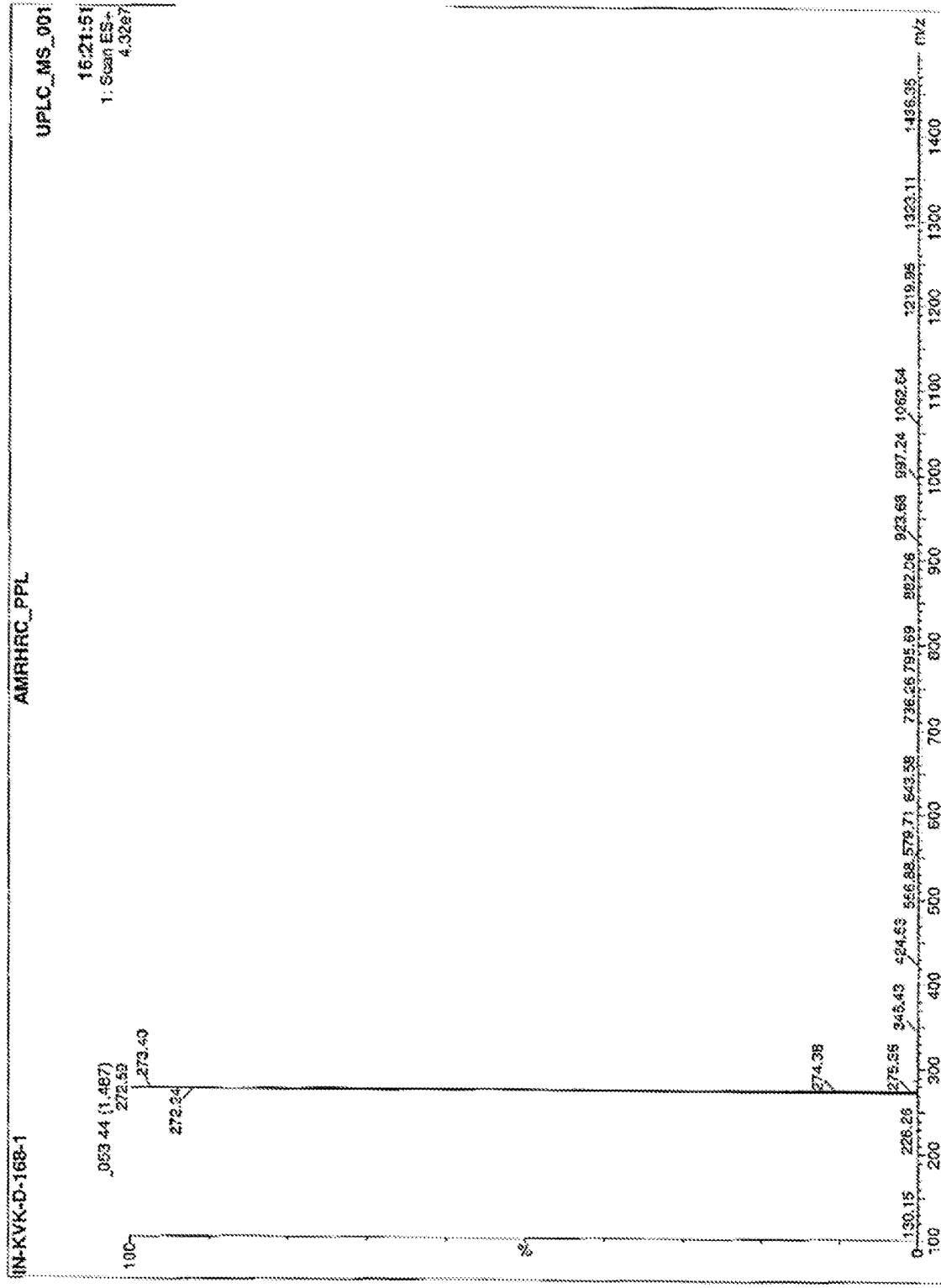
FIG. 14 shows a mass spectrum of delmopinol sodium salt.
Figure 17:
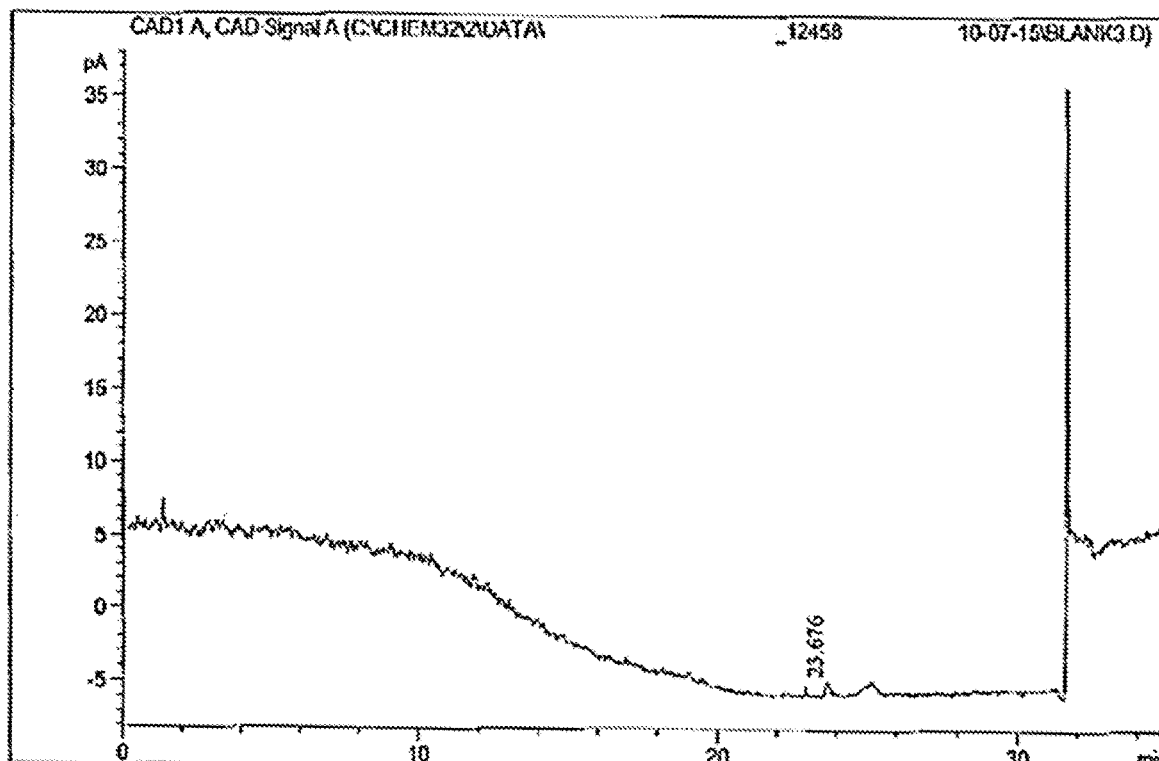
FIG. 17 shows an HPLC chromatogram of blank injection. The detector used was a CAD.
Figure 18:
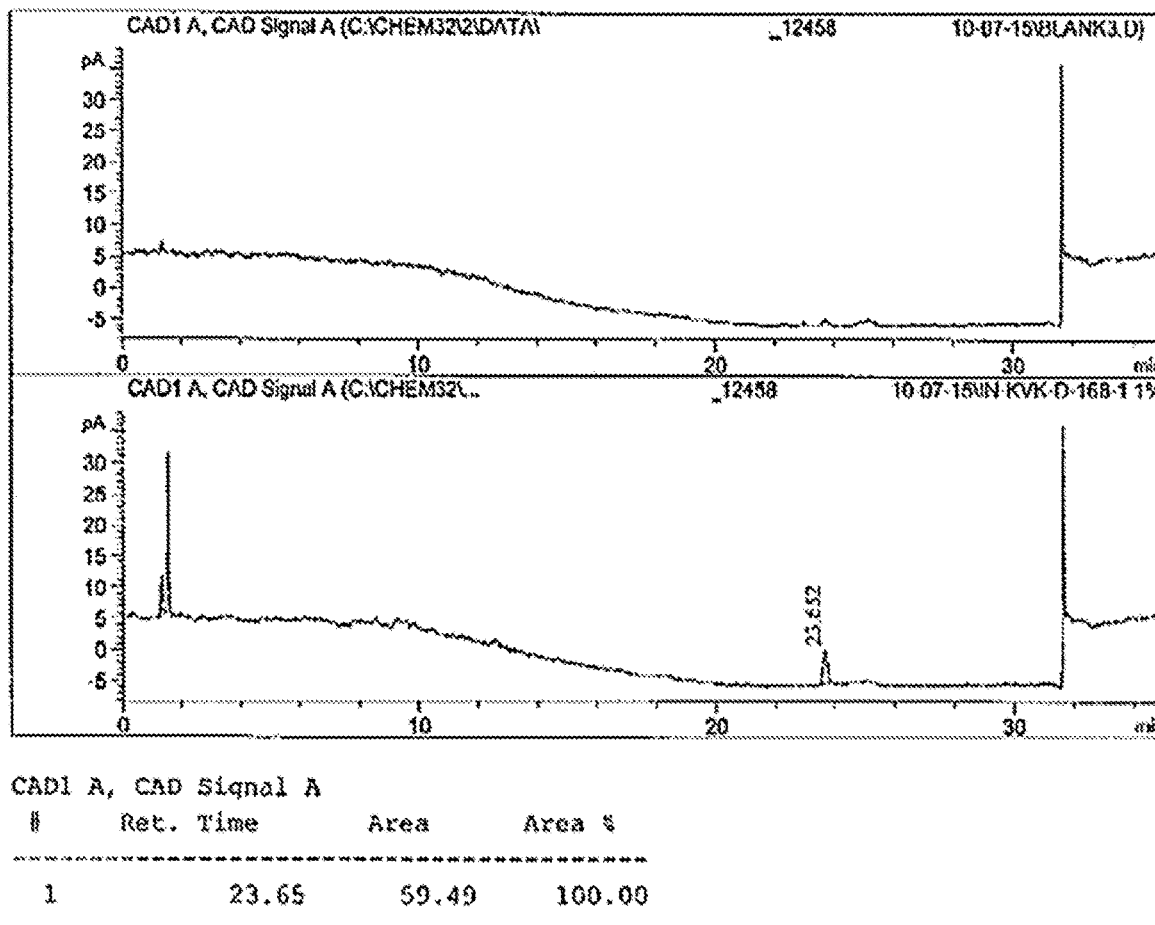
FIG. 18 shows an HPLC chromatogram of delmopinol salt. The detector used was a CAD.
Figure 19:
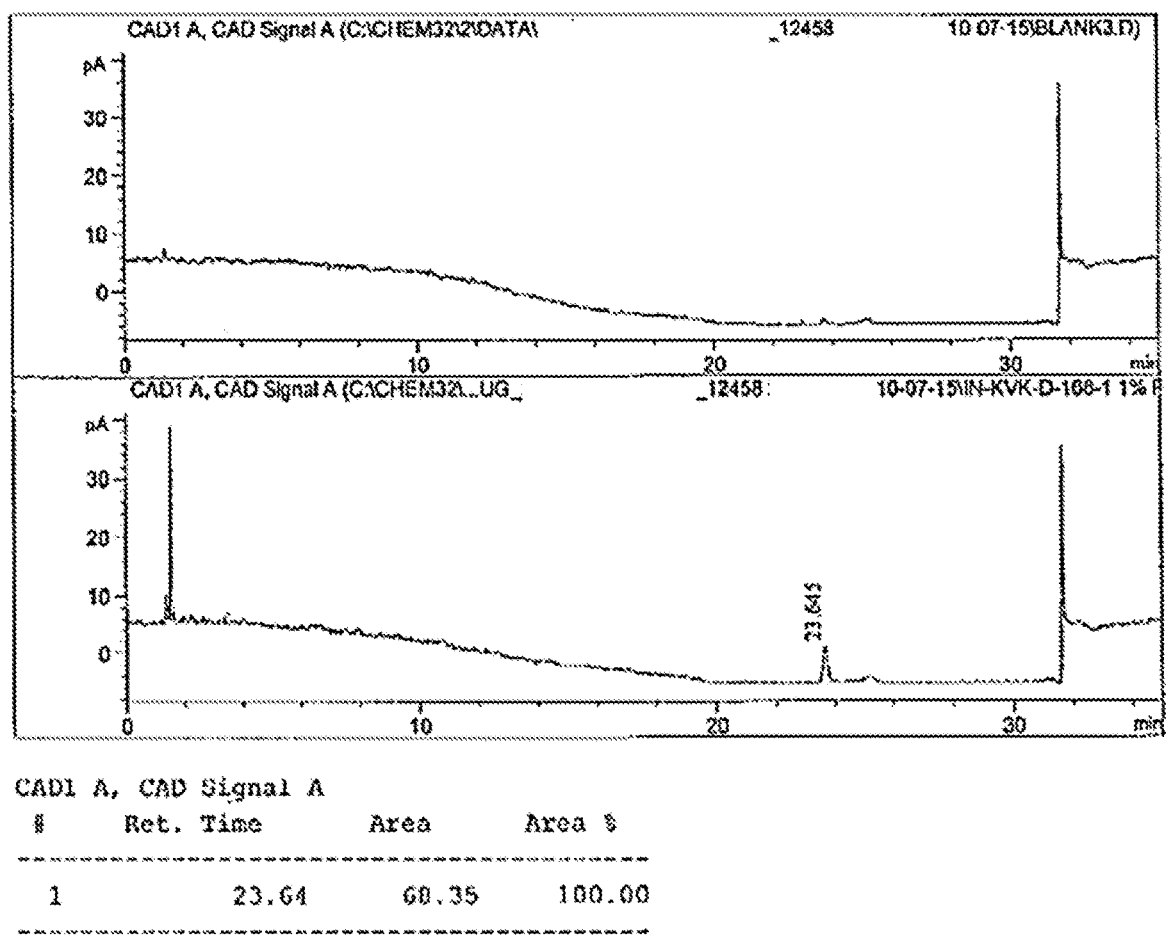
FIG. 19 shows an HPLC chromatogram of delmopinol salt. The detector used was a CAD.
Figure 20:
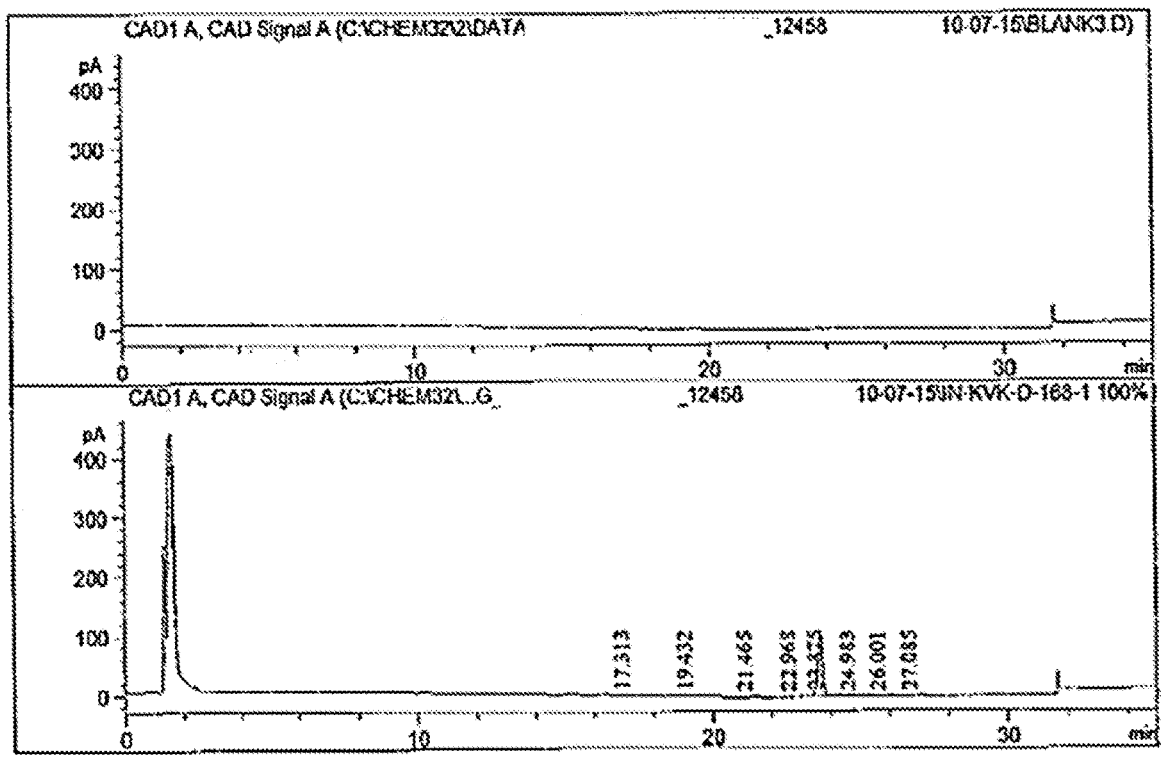
FIG. 20 shows an HPLC chromatogram of delmopinol salt. The detector used was a CAD.
Figure 20:
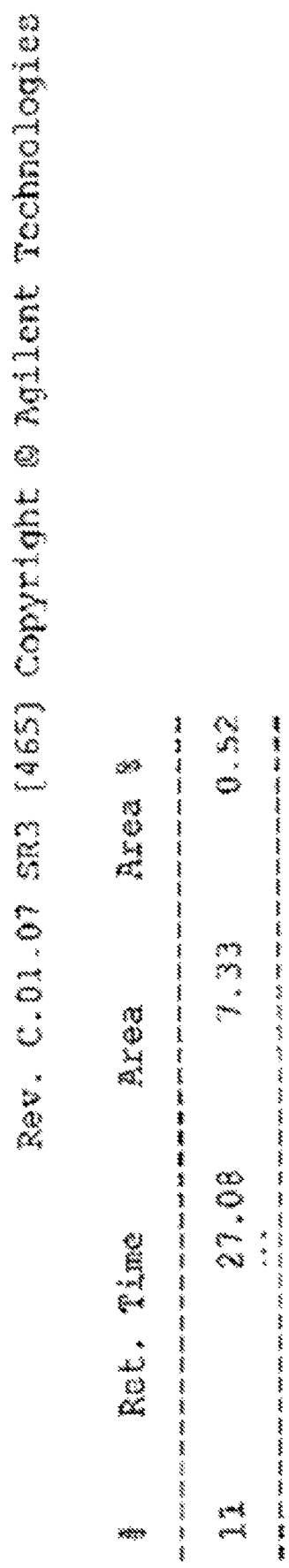
Figure 21:
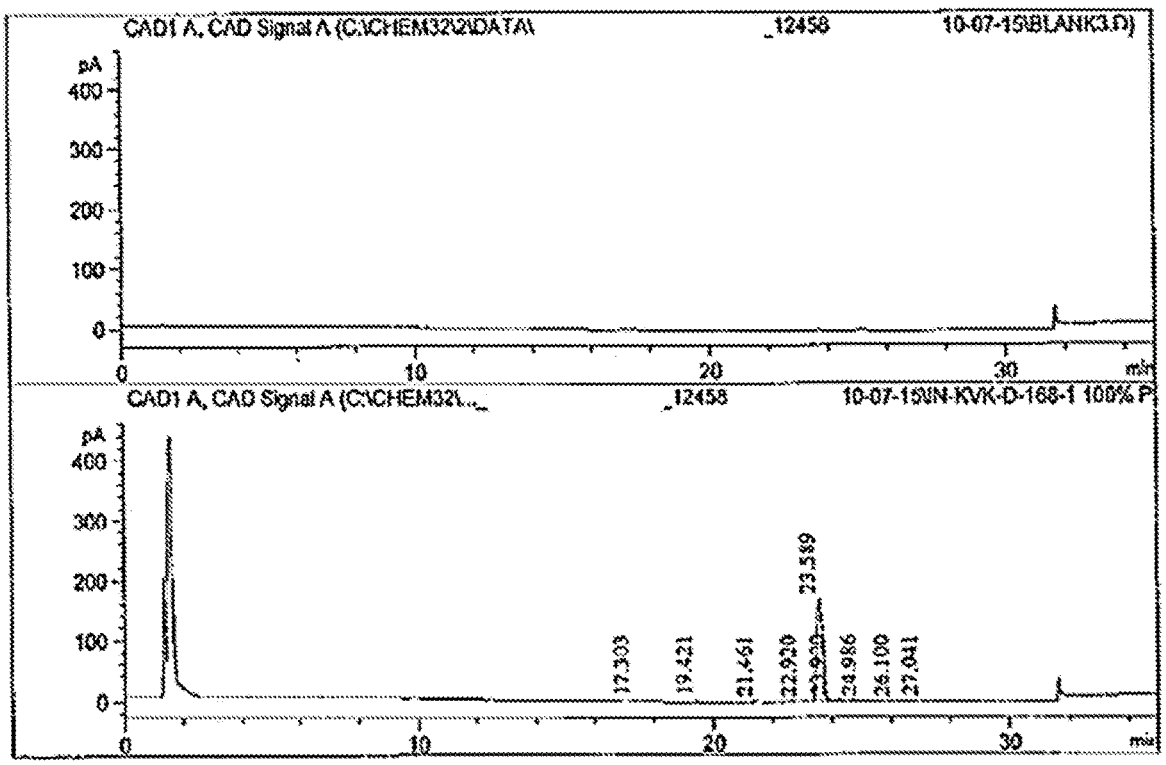
FIG. 21 shows an HPLC chromatogram of delmopinol salt. The detector used was a CAD.

Although claimed subject matter will be described in terms of certain examples, other examples, including examples that do not provide all of the benefits and features set forth herein, are also within the scope of this disclosure. Various structural, logical, and process step, changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

The present disclosure provides methods of making delmopinol and delmopinol salts (e.g., delmopinol metal salts, such as, for example, delmopinol calcium salts, delmopinol sodium salts, delmopinol potassium salts, and/or delmopinol magnesium salts). Delmopinol has the following structure:

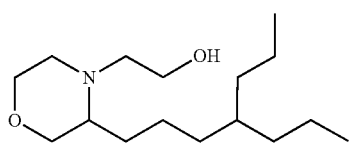 [SMILES: CCCC(CCC)CCCC1COCCN1CCO]

and a salt of delmopinol has the following structure:

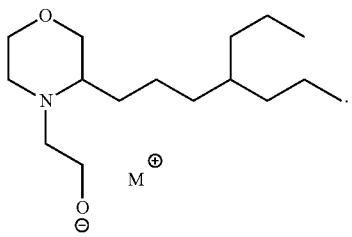

In an aspect, the present disclosure provides methods of making delmopinol and delmopinol salts (e.g., delmopinol calcium salts, delmopinol sodium salts, delmopinol potassium salts, and/or delmopinol magnesium salts). A method of making delmopinol and delmopinol salts (e.g., delmopinol calcium salts, delmopinol sodium salts, delmopinol potassium salts, and/or delmopinol magnesium salts) may comprise: contacting

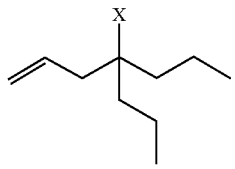

with a first reaction mixture comprising: morpholine, a first solvent, $H_2O_2$, and $Na_2WO_4 \cdot 2H_2O$, where

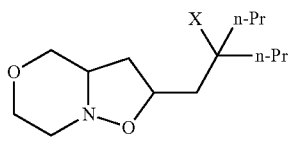

is formed (e.g., reacting

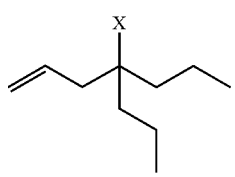

with morpholine, $H_2O_2$ and $Na_2WO_4 \cdot 2H_2O$ in a solvent) and X is an alcohol, an —O⁻, or a protected alcohol (e.g., OTs or the like) contacting

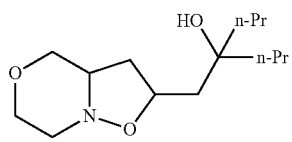

with a second reaction mixture comprising: p-toluenesulfonic acid, a second solvent, $H_2$ gas at a pressure of at least 10 kg/cm², and Pd/C, where

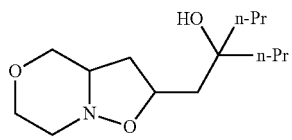

is formed (e.g., reacting

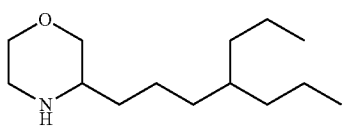 [SMILES: CCCC(CCC)CCCC1COCCN1]

with p-toluenesulfonic acid under hydrogenation conditions (e.g., under a hydrogen pressure with 10% Pd/C) in a solvent); contacting

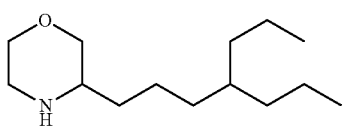 [SMILES: CCCC(CCC)CCCC1COCCN1]

with a third reaction mixture comprising: a third solvent, a salt (e.g., KI, NI, tetrabutylammonium iodide (TBAI), tetrabutylammonium bromide (TBAB), and the like), a base (which is optional), and a halogenated ethyl alcohol (e.g., 2-chloroethanol, 2-bromoethanol), ethylene oxide, or a halogenated ethane comprising a protected alcohol (e.g., OTs or the like) where

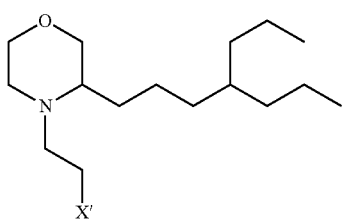

is formed (e.g., reacting

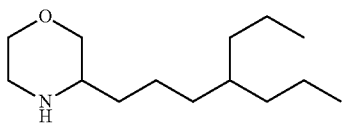 [SMILES: CCCC(CCC)CCCC1COCCN1]

with a salt (e.g., a nucleophilic catalyst, such as, for example KI), a base (e.g., KOH), a halogenated ethyl alcohol (e.g., 2-chloroethanol), a halogenated ethane having a protected alcohol, or ethylene oxide) and X' is an alcohol or a protected alcohol (e.g., OTs or the like); and contacting

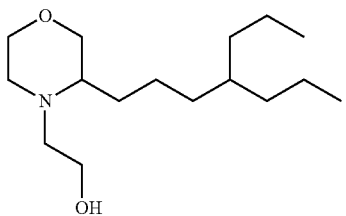 [SMILES: CCCC(CCC)CCCC1COCCN1CCO]

with a metal salt, where

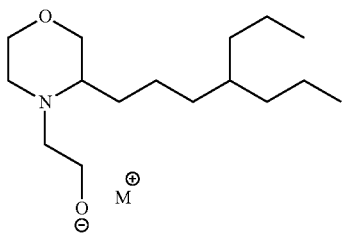

is formed (e.g., reacting

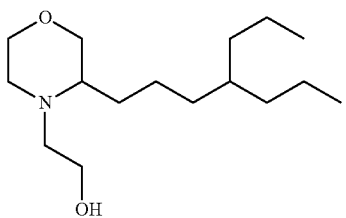 [SMILES: CCCC(CCC)CCCC1COCCN1CCO]

with a metal salt in a solvent (e.g., ethanol)) and M⁺ is a metal cation, with the proviso that the method does not comprise formation of

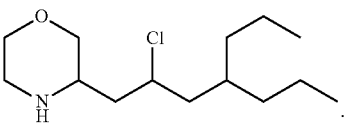 [SMILES: CCCC(CCC)CC(Cl)CC1COCCN1]

A method of the present disclosure does not comprise conversion of i)

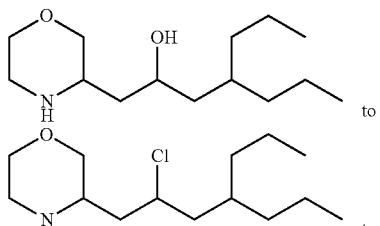

ii)

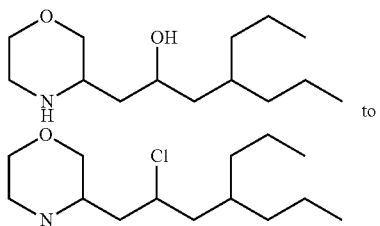

iii)

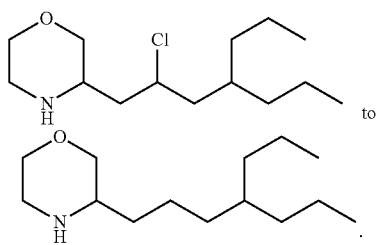

Between various steps (e.g., reactions) of a method of the present disclosure (e.g., after the

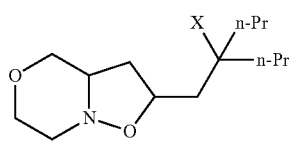

and/or the

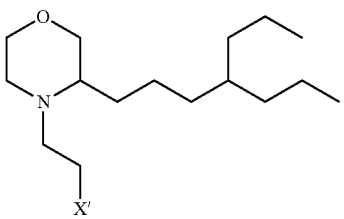

is/are formed) where a protected alcohol is used in lieu of an alcohol, the method may further comprise removing the protecting group (e.g., deprotecting) to yield an alcohol. Various alcohol protecting groups are known in the art (e.g., OTs and the like). Various methods of remove alcohol protecting groups are known in the art.

Various solvents may be suitable for the reactions of a method of the present disclosure. The solvents of the present disclosure may be alcohol-based solvents, such as, for example, methanol, ethanol, isopropanol, propanol, butanol, t-butanol, and the like, and combinations thereof. A solvent may be water, acetic acid, or the like, or a combination of any of the listed solvents. For example, the first solvent is ethanol, methanol, or a combination thereof. For example, the second solvent is isopropanol. For example, the third solvent is ethanol.

Formation of

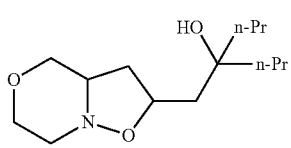

may comprise: i) charging $H_2O_2$ with morpholine, a solvent (e.g., a mixture of ethanol and methanol in a 1:1 v/v ratio), $Na_2WO_4 \cdot 2H_2O$, and

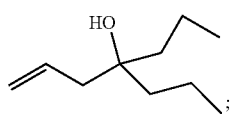

and ii) maintaining the reaction mixture at a first temperature (e.g., 70-80° C., including every 0.1° C. value and range therebetween or 55-100° C., including every 0.1° C. value and range therebetween) for a first period of time (e.g., 15-25 hours, including every 0.01 hour value and range therebetween), where

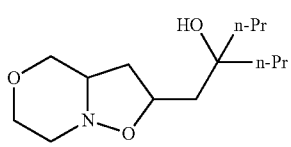

is formed.

In various examples, formation of

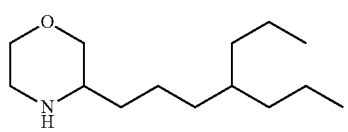 [SMILES: CCCC(CCC)CCCC1COCCN1]

is a one step or two step process. Without intending to be bound by any particular theory, it is expected that the pressure of hydrogen gas in a reaction affects the amount of

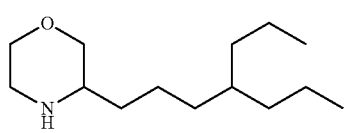 [SMILES: CCCC(CCC)CCCC1COCCN1]

produced from

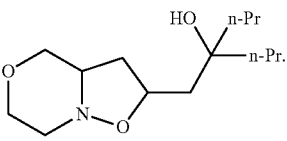

In various examples, where

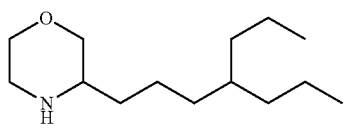 [SMILES: CCCC(CCC)CCCC1COCCN1]

is formed from

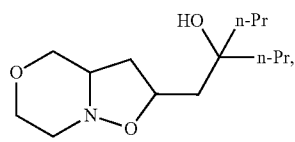

the pressure of hydrogen gas is at least 50 kg/cm². For example, a method to make

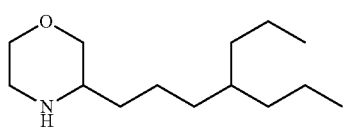 [SMILES: CCCC(CCC)CCCC1COCCN1]

comprises: i) charging

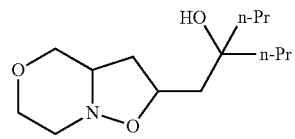

with p-toluenesulfonic acid, Pd/C, and isopropanol in a vessel to form a reaction mixture (e.g., where the reaction mixture is in an autoclave); ii) pressurizing the reaction mixture with hydrogen gas to a pressure of at least 50 kg/cm² at a first temperature (e.g., 25° C.); iii) the reaction mixture is then maintained at a second temperature (e.g., 70-80° C.), where

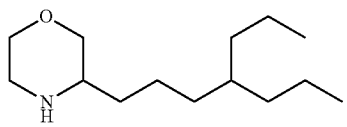 [SMILES: CCCC(CCC)CCCC1COCCN1]

is formed. Formation of

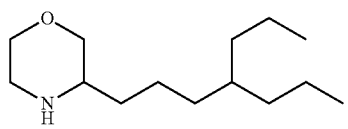 [SMILES: CCCC(CCC)CCCC1COCCN1]

may be followed or tracked via methods known in the art (e.g., HPLC, TLC, and the like).

In various examples,

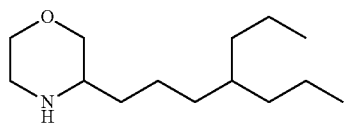 [SMILES: CCCC(CCC)CCCC1COCCN1]

is formed in two steps. The first step of the two steps is:

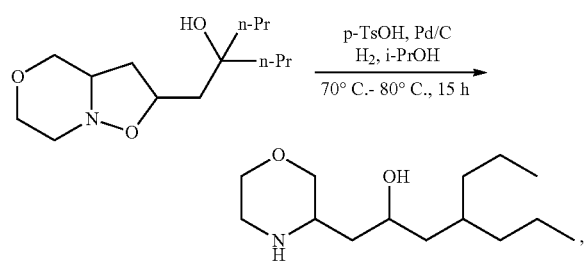

where the pressure of hydrogen is 10-35 kg/cm², including every 0.1 kg/cm² value and range therebetween (e.g., 30 kg/cm²). In various examples, the hydrogen pressure is at least 50 kg/cm². The second step of the two steps is:

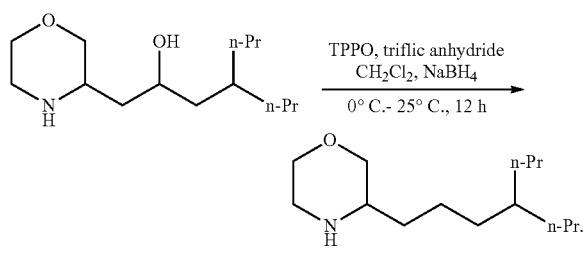

The second step comprises contacting the product of the first step (e.g., 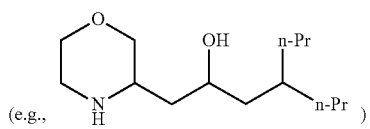)

with a fourth reaction mixture comprising: triphenylphosphine oxide (TPPO); triflic anhydride; a fourth solvent; and a reductant. In various examples, the second step comprises i) charging a solution of TPPO in dichloromethane with triflic anhydride at a first temperature (e.g., 0° C.) to form the fourth reaction mixture; ii) adding the products of the first step to the fourth reaction mixture over a first period of time (e.g., over the course of 60 minutes); and iii) adding NaBH₄ to the fourth reaction mixture iv) maintaining the first temperature for a second period of time (e.g., 30 minutes); v) maintaining the fourth reaction mixture at a second temperature (e.g., 25° C.). In various examples, the temperatures are maintained in their respective steps.

Formation of

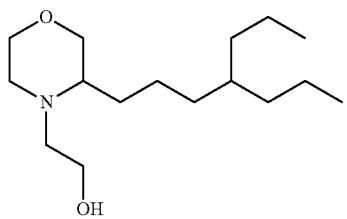

from

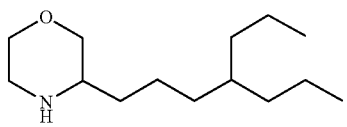 [SMILES: CCCC(CCC)CCCC1COCCN1]

may comprise: i) refluxing a reaction mixture of

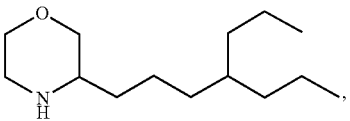 [SMILES: CCCC(CCC)CCCC1COCCN1]

chloroethanol, KI, and a solvent (e.g., ethanol); ii) charging the reaction mixture with a base (e.g., KOH in ethanol), where

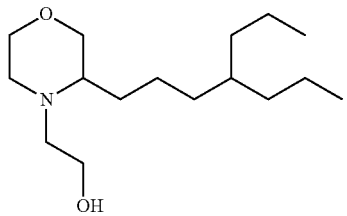

is formed.

Various bases may be suitable for alkylation of the morpholino nitrogen. The bases may be strong bases (e.g., hydroxide bases and the like). An example of a base includes, but is not limited to KOH, NaOH, NaH, CaH₂, n-BuLi, s-BuLi, triethylamine (TEA), diisopropylethylamine (DIPEA), and the like.

Delmopinol salts may be formed by mixing a metal salt (e.g., calcium chloride, sodium carbonate, or the like) with a solution of delmopinol.

Various metal salts may be used to in reactions to convert delmopinol to a delmopinol salt. The metal salts may be calcium salts, potassium salts, magnesium salts, or sodium salts. Examples of calcium salts include, but are not limited to, calcium chloride and the like. Examples of potassium salts include, but are not limited to, potassium carbonate, potassium hydroxide, and the like, and combinations thereof. Examples of sodium salts include, but are not limited to, sodium carbonate, sodium bicarbonate, sodium hydroxide, sodium methoxide, and the like, and combinations thereof. Examples of magnesium salts include, but are not limited to, magnesium chloride and the like. In various examples, the delmopinol salt may be produced by treating delmopinol with a metal hydride. Suitable examples of metal hydrides include, but are not limited to, sodium hydride.

Any one or all of the reactions of a method of the present disclosure may comprise various workup, isolation, purification steps, and/or any combination thereof. For example, a reaction of the present disclosure further comprise a workup, an isolation, purification, or any combination thereof. Examples of these steps include, but are not limited to washing with brine, washing with an acid and/or base, extracting with an organic solvent (e.g., ethyl acetate, dichloromethane, or the like), column chromatography, and the like, and combinations thereof. Additional methods of workup, isolation, and purification steps are known in the art and may be applied to reactions of a method of the present disclosure.

The steps of the method described in the various examples disclosed herein are sufficient to carry out the methods of the present disclosure. Thus, in an example, a method consists essentially of a combination of the steps of the methods disclosed herein. In another embodiment, the method consists of such steps.

The following Statements present various embodiments of the present disclosure.

Statement 1. A method of making a delmopinol salt, comprising: (I) contacting

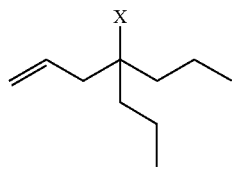

with a first reaction mixture comprising: (i) morpholine, (ii) a first solvent, (iii) H₂O₂, and (iv) Na₂WO₄.2H₂O, wherein

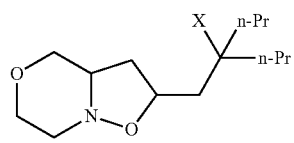

is formed and X is an alcohol or protected alcohol; (II) contacting the

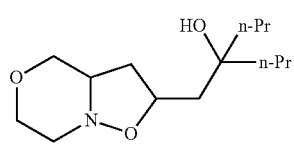

with a second reaction mixture comprising: (i) p-toluenesulfonic acid, (ii) a second solvent, (iii) H₂ gas at a pressure of at least 10 kg/cm², and (iv) Pd/C, wherein

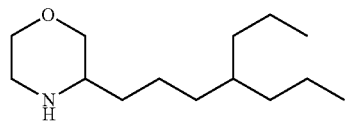 [SMILES: CCCC(CCC)CCCC1COCCN1]

is formed; (III) contacting the

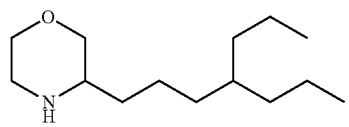 [SMILES: CCCC(CCC)CCCC1COCCN1]

with a third reaction mixture comprising: (i) a third solvent, (ii) a salt, (iii) a halogenated ethyl alcohol, ethylene oxide, or a halogenated ethane having a protected alcohol, and (iv) optionally, a base, wherein

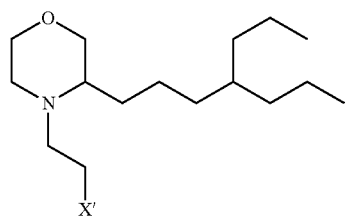

is formed and X' is an alcohol, protected alcohol, or halogen, and (IV) contacting the

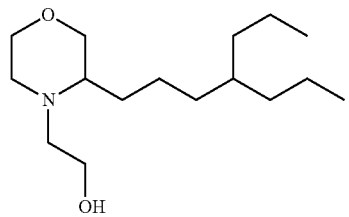

with a metal salt, wherein

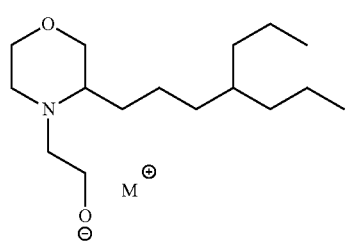

is formed and M⁺ is a metal cation (e.g., sodium, calcium, or the like), with the proviso that the method does not comprise formation of

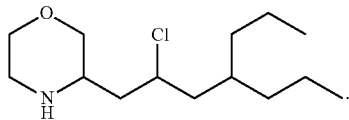 [SMILES: CCCC(CCC)CC(Cl)CC1COCCN1]

Statement 2. A method according to Statement 1, further comprising removing the protecting group of the protected alcohol after the

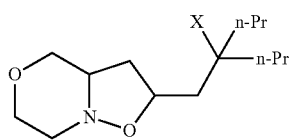

and/or the

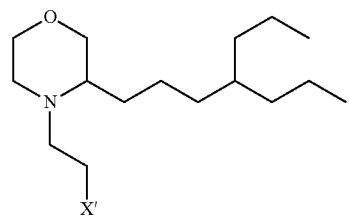

is/are formed.

Statement 3. A method according to Statements 1 or 2, where the first solvent is an alcohol (e.g., ethanol, methanol, or a mixture thereof, and the like), acetic acid, or water.

Statement 4. A method according to any one of the preceding Statements, where the second solvent is an alcohol (e.g., methanol, ethanol, isopropanol, and the like), acetic acid, or water.

Statement 5. A method according to any one of the preceding Statements, where the third solvent is an alcohol (e.g., methanol, ethanol, isopropanol, and the like), acetic acid, or water.

Statement 6. A method according to any one of the preceding claims, where the base is chosen from KOH, NaOH, NaH, CaH₂ n-BuLi, s-BuLi, and the like, and combinations thereof.

Statement 7. A method according to any one of the preceding Statements, where the salt is chosen from KI, NaI, tetrabutylammonium iodide (TBAI), tetrabutylammonium bromide (TBAB), and the like, and combinations thereof.

Statement 8. A method according to any one of the preceding Statements, where the metal salt chosen from sodium salts (e.g., sodium carbonate), potassium salts (e.g., potassium carbonate), magnesium salts (e.g., magnesium chloride), and calcium salts (e.g., calcium chloride).

Statement 9. A method according to any one of the preceding Statements, where

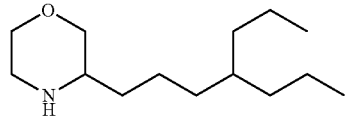 [SMILES: CCCC(CCC)CCCC1COCCN1]

is formed in one step.

Statement 10. A method according to Statement 9, where the contacting the

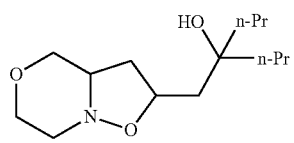

comprises pressurizing to at least 50 kg/cm² (e.g., pressurizing to 50 kg/cm² in the presence of p-toluenesulfonic acid).

Statement 11. A method according to any one of the Statements 1-8, where

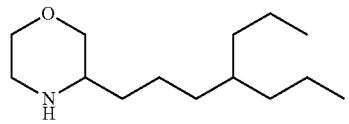

is formed in two steps (e.g., a first step and a second step).

Statement 12. A method according to Statement 11, where the first step is contacting the

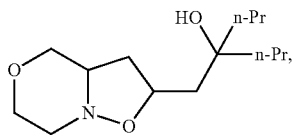

where the second reaction mixture further comprising

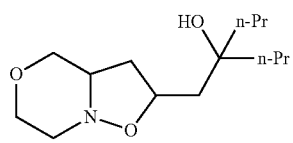

is pressurized to 10-35 kg/cm².

Statement 13. A method according to Statements 11 or 12, where the second step comprises contacting the product(s) of the first step to a fourth reaction mixture comprising: (i) triphenylphosphine oxide (TPPO); (ii) triflic anhydride; (iii) a fourth solvent; and (iv) a reductant, where

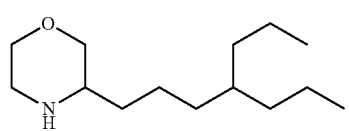 [SMILES: CCCC(CCC)CCCC1COCCN1]

is formed.

Statement 14. A method according to Statement 13, where the fourth solvent is chosen from dichloromethane, chloroform, 1,2-dichloroethane, chlorobenzene, and the like, and combinations thereof.

Statement 15. A method according to Statement 13 or Statement 14, where the reductant is chosen from $NaBH_4$, $LiBH_4$, $NaBH_3CN$, $LiAlH_4$, $NaBH(OAc)_3$, and the like.

Statement 16. A method according to any one of Statements 13-15, where the second step comprises: i) charging a solution of TPPO in dichloromethane with triflic anhydride at a first temperature (e.g., 0° C.) to form the fourth reaction mixture; ii) adding the products of the first step to the fourth reaction mixture over a first period of time (e.g., over the course of 60 minutes); iii) adding $NaBH_4$ to the fourth reaction mixture; iv) maintaining the first temperature for a second period of time (e.g., 30 minutes); and v) maintaining the fourth reaction mixture at a second temperature (e.g., 25° C.).

Statement 17. A method of any one of the preceding Statements, further comprising a workup (e.g., washing with brine, extracting with a suitable organic solvent, combinations thereof, and the like), isolation, and/or purification step (e.g., column chromatography).

The following examples are presented to illustrate the present disclosure. They are not intended to be limiting in any matter.

Example 1

This example provides a description a method of the present disclosure.

Synthesis of Delmopinol Sodium salt was achieved in six steps starting from the commercially available heptanone. The synthetic scheme is listed below.

Scheme 1. Synthesis of Delmopinol sodium salt.

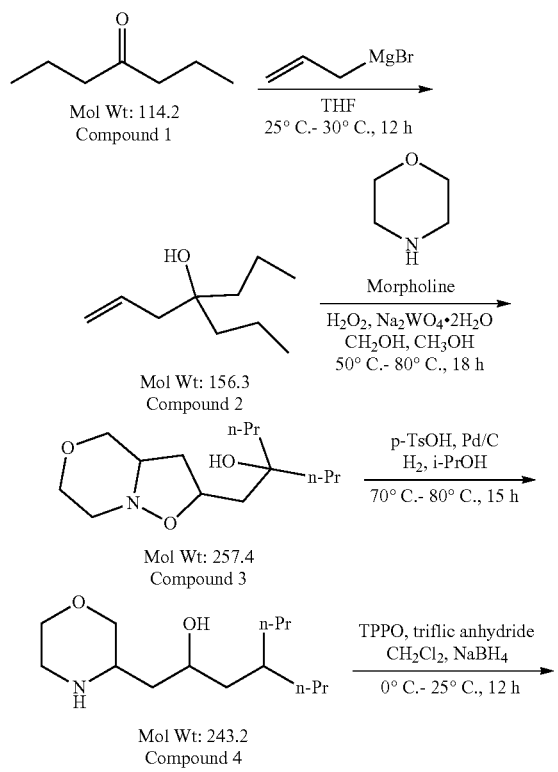

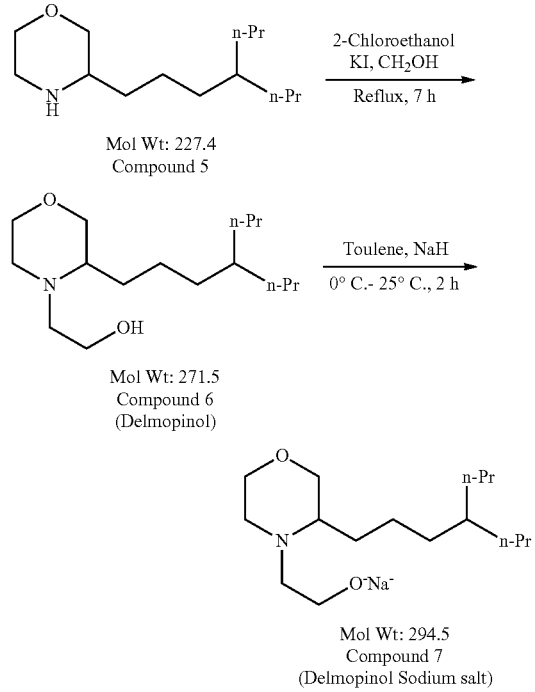

Safety: Based on the structure, compound 3 is a high energetic compound and might be temperature sensitive. Hence, DSC of compound 3 was tested before scaling up.

The test results for this sample were summarized in Table 1.

TABLE 1

| | DSC Test Results | |
|---|---|---|
| Material Tested | $T_{onset}$ (° C.) | ΔH (J/g) |
| Stage-2 Reaction Mass | >41 | 882 |
| Compound 3 | >99 | 934 |
| Stage-3 Reaction Mass | >123 | −318 |
| Compound 4 | >65 | 154 |

The DSC data of the following shows that compound 3 is a highly energetic molecule, also having a lower onset temperature. To counter the issue, $H_2O_2$ addition temperature and speed was reduced during stage-2 reactions.

Step 1: Preparation of compound 2. The reaction was scaled up. The results were summarized in Table 2.

TABLE 2

| Preparation of compound 2. | | | |
|---|---|---|---|
| Input: compound 1 | Output: compound 2 | | |
| Mass (g) | Mass (g) | Yield (%) | $^1$H NMR |
| Heptanone (200) | 258 | 94.1 | Complies |
| Heptanone (500) | 960 | 70.0 | Complies |
| Heptanone (500) | | | |
| Heptanone (200) | 460 | 84.0 | Complies |
| Heptanone (200) | | | |

Step 2: Preparation of compound 3. The reaction was scaled up following a small-scale run. The results for the scale-up reactions are outlined in Table 3.

TABLE 3

Preparation of compound 3.

| Input: Compound 2 | Output: Compound 3 | | |
|---|---|---|---|
| Mass (g) | Mass (g) | Yield (%) | $^1$H NMR |
| 50.0 | 37.0 | 45.1 | Complies |
| 50.0 | 36.0 | 21.9 | Complies |
| 50.0 | | | |
| 50.0 | 37.0 | 22.5 | Complies |
| 50.0 | | | |
| 100 | 150 | 45.7 | Complies |
| 100 | | | |
| 150 | 220 | 44.7 | Complies |
| 150 | | | |

Step 3: Preparation of compound 4. The reaction was scaled up following a a small-scale run. The results for the scale-up reactions were outlined in Table 4.

TABLE 5

Preparation of compound 4.

| Input: compound 3 | Output: compound 4 | | |
|---|---|---|---|
| Mass (g) | Mass (g) | Yield (%) | $^1$H NMR |
| 40.0 | 19.1 | 50.5 | Complies |
| 130 | 62 | 50.4 | Complies |
| 150 | 38 | 26.7 | Complies |
| 150 | 30 | 21.1 | Complies |
| 180 | 65 | 38.1 | Complies |

Step 4: Preparation of compound 5. This conversion is a new method to prepare compound 5. The reaction was scaled up. The results were summarized in Table 5.

TABLE 5

Preparation of compound 5

| Input: compound 4 | Output: compound 5 | | |
|---|---|---|---|
| Mass (g) | Mass (g) | Yield (%) | $^1$H NMR |
| 40 | 16 | 42.8 | Complies |
| 38 | 25 | 70.4 | Complies |
| 45 | 28 | 66.6 | Complies |
| 30 | 12 | 42.8 | Complies |

Step 5: Preparation of compound 6. This method is a new method to prepare compound 6. The reaction was scaled up following a small-scale run. The results for the scale-up reactions were outlined in Table 6.

TABLE 6

Preparation of compound 6

| Input: compound 3 | Output: compound 4 | | |
|---|---|---|---|
| Mass (g) | Mass (g) | Yield (%) | $^1$H NMR |
| 10.0 7.00 | 6.30 | 31.0 | Complies |
| 10.0 | 6.10 | 51.2 | Complies |
| 22.5 | 19.0 | 70.7 | Complies |
| 8.00 | 5.00 | 52.3 | Complies |
| 13.0 | 8.00 | 51.5 | Complies |

Step 6: Preparation of compound 7. The compound 7 was prepared as a new derivative of Delmopinol for first time. The reaction was scaled up successfully following a small-scale run. The results for the scale-up reactions were outlined in Table 7.

TABLE 7

Preparation of compound 7.

| Input: compound 3 | Output: compound 4 | | |
|---|---|---|---|
| Mass (g) | Mass (g) | Yield (%) | $^1$H NMR |
| 0.20 g | 0.12 g | 55.5 | Complies |
| 0.50 g | 0.14 g | 25.9 | Complies |
| 5.00 | 3.2 | 58.9 | Complies |

Laboratory grade reagents were purchased and were used as received. $^1$H NMR and $^{13}$C NMR spectra were obtained on a Bruker AVANCE 400 Ultra Shield spectrometer at 400 MHz (for $^1$H NMR) and 100 MHz (for $^{13}$C NMR) with tetramethylsilane used as an internal reference. Thin Layer chromatography (TLC) was performed using Whatman No. 4500-101 (Diamond No. MK6F silica-gel 60 Å) plates. HPLC analyses were performed on an Agilent 1100 Series Instrument. The mass spectra were obtained on a Finnigan LCQ-DUO spectrometer using electrospray ionization.

Preparation of compound 2. 4-Heptanone (400 g, 3.5 mol) in dry THF (3600 mL) was slowly charged to a solution of allyl magnesium bromide (1 M) in THF (5250 mL, 1.5 equiv) at 25° C. The reaction mixture was observed as slight exothermic. Upon the addition, the reaction mixture was maintained at 30° C. for 12 h. Progress of the reaction was monitored by TLC using 5% MeOH:CH$_2$Cl$_2$. The reaction mixture was poured on a mixture of ice (560 g), NH$_4$Cl (1600 mL of 20%) and HCl (1200 mL of 5 M). The ether phase was separated and the water phase was extracted with MTBE (3×1000 mL). The combined organic phases were dried over Na$_2$SO$_4$ and were evaporated. The resultant product was crude compound, which was purified by silica gel (100-200 mesh) and was eluted with 3% MeOH:CH$_2$Cl$_2$ to afford Compound 2 (460 g, 84%) as pale yellow liquid. The compound afforded was used in the next step.

Preparation of compound 3. H$_2$O$_2$ (651.0 mL, 5.76 mol of 35%) was charged to a mixture of morpholine (250 g, 2.88 mol), methanol (990 mL), ethanol (990 mL), 4-hydroxy-4-propyl-1-heptene (150 g, 0.96 mol) and Na$_2$WO$_4$.2H$_2$O (31.6 g, 0.096 mol) at 50-80° C. The mixture was maintained at 50-60° C. for 18 h. The reaction mixture was cooled down to 25° C. EtOAc (600 mL), water (600 mL) was added to the reaction mixture and the mixture was extracted with EtOAc (2×1000 mL). The organic phase was treated with HCl (5 M), extracted with (4×200 mL) and starting material (23.5 g) was recovered. The acidic aqueous phase was alkalized and was extracted with EtOAc. The reaction mixture was dried with Na$_2$SO$_4$ and evaporated to obtain desired product. The resultant product obtained was crude compound, which was purified by silica gel (100-200 mesh) and was eluted with 4% MeOH:CH$_2$Cl$_2$ to afford Compound 3 (220 g, 44.7%) as pale yellow liquid. The compound afforded was used in the next step.

Preparation of compound 4. Compound 3 (180 g, 699 mol), p-toluene sulfonic acid (486 g, 2.55 mol) and Pd—C (27.0 g of 10%) in isopropanol (1300 mL) was shaken in an autoclave (5.0 L) at 70-80° C. and hydrogen pressure (30 kg/cm$^2$) for 15 h. Upon cooling, the reaction mixture was filtered and the isopropanol was evaporated in a good vacuum. NaOH (5 M excess) was added to the reaction mixture and the mixture was extracted with EtOAc. The organic layer was dried over sodium sulphate and was concentrated to obtain crude compound. The crude was purified by silica gel column (100-200 mesh) using 4% MeOH in CH$_2$Cl$_2$ to afford compound 4 (65.0 g, 38.1%) as light yellow liquid.

Preparation of compound 5. To a solution of TPPO (86.9 g, 0.31 mol) in CH$_2$Cl$_2$ (570 mL) at 0° C. under nitrogen was charged with a triflic anhydride (57.2 g, 0.2 mol) diluted in CH$_2$Cl$_2$ (483 mL) dropwise over ~30-60 min. At 0° C., after 5 min the addition was completed. Compound 5 (38.0 g, 0.15 mol) was dissolved in CH$_2$Cl$_2$ (483 mL) was added over 60 min (slight exothermic to 2° C.). Five min after the addition was completed, NaBH$_4$ (29.5 g, 0.78 mol) was added in a single lot. The reaction mixture was maintained for 30 min at 0° C. and the reaction mixture was maintained for 12 h at 25° C. Upon that reaction was monitored by TLC to check reaction completion. Once the reaction was completed it was quenched into HCl (1 N) aqueous solution (1000 mL) at 0° C. Organic layer was separated and the aqueous layer was extracted with CH$_2$Cl$_2$ (3×200 mL). The combined organic layer was washed with brine (1 L), was dried with Na$_2$SO$_4$, filtered and was concentrated under vacuum. The resultant product was crude compound, which was purified by silica gel (100-200 mesh) and was eluted with 4% MeOH: CH$_2$Cl$_2$ to afford compound 5 (25.0 g, 70.4%) as light yellow liquid. The compound afforded was used in the next step.

Preparation of compound 6. A mixture of Compound 5 [22.5 g, 0.1 mol, AMRI lot #IN-SPM-B-50 (Pure)], chloroethanol (31.7 g, 0.39 mol), potassium iodide (9.8 g, 0.059 mol) and ethanol (63 mL) was refluxed to 5 h. KOH (4.00 g) in ethanol (20 mL) was added to the reaction mixture and continued reflux to 2 h. Followed by second addition of KOH (2.50 g) in ethanol (11.0 mL) to the reaction mixture. The reaction mixture was refluxed to 7 h was followed by a third addition of KOH (2.00 g) in of ethanol (10 mL). Upon the reaction mixture was refluxed to another 2 h, the solvent was evaporated and water (10 mL) was added to the reaction mixture. The mixture was extracted with CH$_2$Cl$_2$ (3×50 mL) and the combined organic phases were washed with brine solution (225 mL). Upon the reaction mixture was dried and was evaporated to obtain 3-(4-propylheptyl)-4-morpholine-ethanol [26.5 g (crude) Delmopinol] was isolated. The resultant product was crude compound was purified by silica gel (100-200 mesh) and was eluted with 4% MeOH:CH$_2$Cl$_2$ to afford compound 6 (19.0 g, 70.7%) as light yellow liquid.

Preparation of compound 7. To a stirred solution of compound 6 (5.00 g, 0.01845 mol) in toluene, sodium hydride (60%) dispersion in mineral oil (0.74 g, 0.01845 mol) was added at 0° C. and maintained for 10 min. Upon the reaction mass was gradually heated at 25° C. and again maintained for 2 h. The reaction mass was concentrated under vacuum at 45-50° C. to remove complete toluene traces. The product was stirred with hexane and settled for 10-15 min. The upper hexane layer was decanted and the product was dried under vacuum to afford compound 7 (3.20 g, 58.9%) as off-white solid.

Example 2

This example provides details of the procedures followed for the synthesis of Delmopinol calcium salt and Delmopinol sodium salt.

Synthesis of Delmopinol salts (Ca & Na) were achieved in five steps starting from the commercially available heptanone. The synthetic scheme was given below.

Scheme 2. Synthesis of Delmopinol salt.

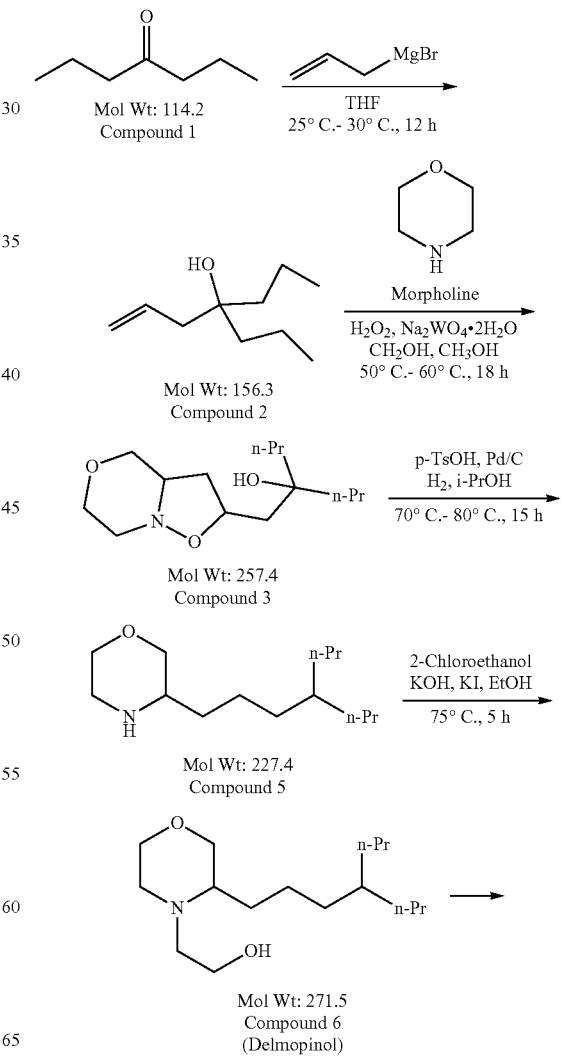

-continued

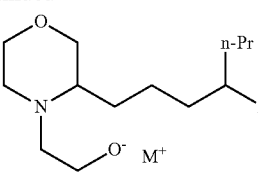

Mol Wt: 294.5
Compound 7
(Delmopinol salt)

The procedure for the preparation of Delmopinol salts (Ca & Na) under non-GMP conditions. All the reported purities were determined by GC and HPLC-CAD.

Step 1: Preparation of Compound 2.

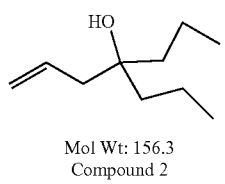

Mol Wt: 114.2
Compound 1

$\xrightarrow[25° C.- 30° C., 12 h]{THF}$

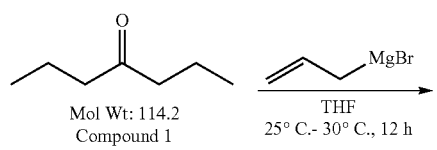

Mol Wt: 156.3
Compound 2

The procedure for the conversion of compound 1 to 2 was scaled up. The results were summarized in Table 8.

TABLE 8

Preparation of Compound 2.

| Compound 1 | Compound 2 | | | |
|---|---|---|---|---|
| Mass (g) Source | Mass (g) | Purity (%) | Yield (%) | Comments/Analysis |
| 50.0 | 70.0 (crude) | | 99.0 | The crude product was confirmed by $^1$H NMR. |
| 1200 | 1160 | | 70.6 | Crude was purified by column chromatography. Product was confirmed by $^1$H NMR. |
| 1200 | 1170 | | 71.2 | Crude was purified by column chromatography. Product was confirmed by $^1$H NMR. |

Step 2: Preparation of Compound 3.

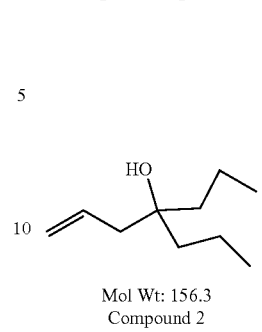 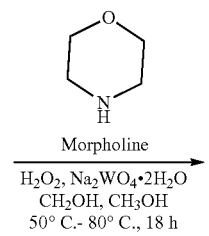

Mol Wt: 156.3
Compound 2

Morpholine
$\xrightarrow[\substack{H_2O_2, Na_2WO_4 \cdot 2H_2O \\ CH_2OH, CH_3OH \\ 50° C.- 80° C., 18 h}]{}$

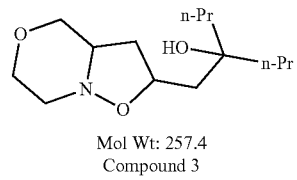

Mol Wt: 257.4
Compound 3

The reaction was scaled up. The results were summarized in Table 9.

TABLE 9

Preparation of Compound 3.

| | Compound 3 | | |
|---|---|---|---|
| Compound 2 Mass (g) | Mass (g) | Yield (%) | Comments/Analysis |
| 50.0 | 15.0 | 18.5 | The crude was purified by column chromatography. Product was confirmed by $^1$H NMR. |
| 250 | 59.0 | 14.3 | The crude was purified by column chromatography. |
| 250 250 | 134 | 16.2 | Upon completion of reaction, combined two batches reaction mixture and worked up. The crude was purified by column chromatography. Product was confirmed by $^1$H NMR. |
| 250 250 | 120 | 14.5 | Upon completion of reaction, combined two batches reaction mixture and worked up. The crude was purified by column chromatography. Product was confirmed by $^1$H NMR. |
| 300 300 | 187 | 18.9 | Upon completion of reaction, combined two batches reaction mixture and worked up. The crude was purified by column chromatography. Product was confirmed by $^1$H NMR. |
| 250 250 | 133 | 16.1 | Upon completion of reaction, combined two batches reaction mixture and worked up. The crude was purified by column chromatography. Product was confirmed by $^1$H NMR. |

Step 3: Preparation of Compound 5.

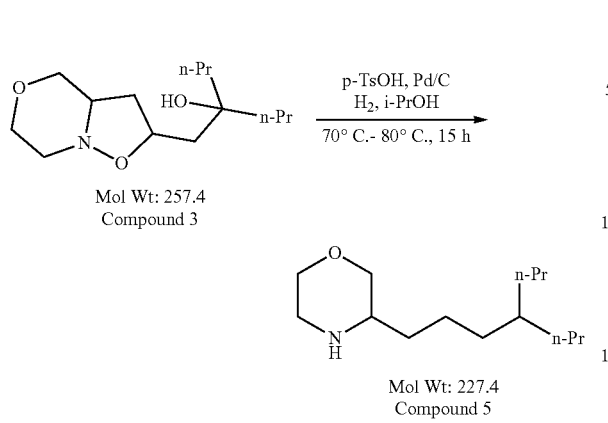

Mol Wt: 257.4
Compound 3

Mol Wt: 227.4
Compound 5

The procedure for the conversion of compound 3 to 5 was developed by a new method. Opening of five membered ring and de-hydroxylation in one step, previously it was two steps and used the expensive reagent triflic anhydride. The results were summarized in Table 10.

TABLE 10

Preparation of Compound 5.

| Compound 3 | Compound 5 | | |
|---|---|---|---|
| Mass (g) | Mass (g) | Yield (%) | Comments/Analysis |
| 13.0 | 4.0 | 34.8 | The crude was purified by column chromatography. Product was confirmed by $^1$H NMR. |
| 190.0 | 65.0 | 38.7 | The crude was purified by column chromatography. Isolated 65.0 g as pure compound and 70 g of $2^{nd}$ crop was isolated. Product was confirmed by $^1$H NMR. |
| 187 120 | 100 | 36.8 | The crude was purified by column chromatography. Product was confirmed by $^1$H NMR. |
| 133 | 55 | 46.8 | The crude was purified by column chromatography. Product was confirmed by $^1$H NMR. |
| 70 | 11.0 | 17.7 | The mixture of compound 5, $2^{nd}$ crop was taken with lot # (IN-SPM-197-2) for further conversion. The crude was purified by column chromatography. Product was confirmed by $^1$H NMR. |

Step 4: Preparation of Compound 6 (delmopinol base).

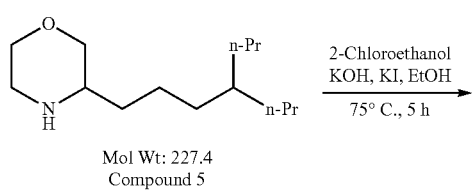

Mol Wt: 227.4
Compound 5

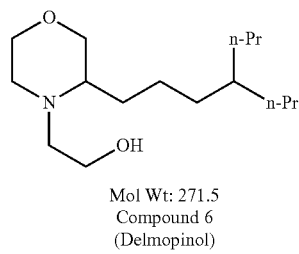

Mol Wt: 271.5
Compound 6
(Delmopinol)

The reaction was scaled up. The results were summarized in Table 11.

TABLE 11

Preparation of Compound 6.

| Compound 5 | Compound 6 | | |
|---|---|---|---|
| Mass (g) | Mass (g) | Yield (%) | Comments/Analysis |
| 4.0 65.0 | 30.0 | 36.4 | The crude was purified by column (amino silica gel) chromatography. Product was confirmed by $^1$H NMR. |
| 100 | 54.0 (94.6%) | 45.2 | Reaction was successful, isolated the pure product. 25.0 g of mixture was isolated. |
| 13 | 3.50 (96.9%) & 6.50 (93.9%) | 76.9 | The Delmopinol base re-purified via column chromatography by using amino silica gel. |
| 22 | 16 (96.2) | 72.7 | The Delmopinol base re-purified via column chromatography by using amino silica gel. |
| 47.5 (Multiple lots mixed to make one single lot) | 16.0 (95.3%) 7.00 95.27%) & 11.0 (97.08%) | 71.5 | The multiple lots of Delmopinol free base was mixed together and re-purified via column chromatography by using amino silica gel. |
| 55.0 | 37.0 | 56.3 | Reaction was successful, isolated the pure compound. $^1$H NMR was consistent. |
| 11.0 | 5.5 | 41.8 | Reaction was successful, isolated the pure compound. $^1$H NMR was consistent. |
| 20.0 | 6.00 (95.8%) & 9.00 (95.9%) | 75.0 | The Delmopinol base was re-purified via column chromatography by using amino silica gel. |
| 11.0 | 6.00 (95.8%) & 3.00 (95.1%) | 81.8 | The Delmopinol base was re-purified via column chromatography by using amino silica gel. |

Step 5: Preparation of Delmopinol Salt (Ca & Na).

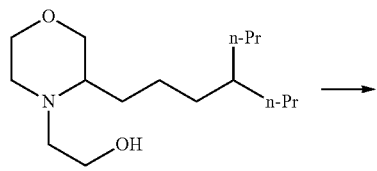

Mol Wt: 271.5
Compound 6
(Delmopinol)

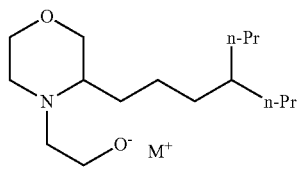

Mol Wt: 294.5
Compound 7
(Delmopinol salt)

The procedure for the conversion of compound 6 to 7 (Delmopinol Calcium salt and Delmopinol Sodium salt) developed both the salts for first time. These are thus new methods for the synthesis of Delmopinol Calcium salt and Sodium salt. The reactions were scaled up successfully and the products were observed as hygroscopic solids. The results were summarized in Table 12 (Delmopinol Calcium salt) and Table 13 (Delmopinol Sodium salt).

TABLE 12

Preparation of Delmopinol calcium salt.

| Compound 6 | Delmopinol Ca Salt | |
|---|---|---|
| Mass (g) | Mass (g) | Comments/Analysis |
| 6.0 | 7.0 | Solvent was distilled at 40° C. to give the solid, HPLC purity: 95.16% |
| 10.0 | 12.0 | Solid isolated, HPLC purity: 95.09% |
| 3.5 | 4.0 | Isolated salt HPLC purity: 97.05% |
| 16.0 | 19.0 | Isolated salt HPLC purity: 95.7% |
| 7.00, 12.0, 4.00, & 19 | 40.0 | Blended four lots of calcium salt and submitted to CAD HPLC; purity: 96.24% Lot No. IN-KVK-D-144-1 |

TABLE 13

Preparation of delmopinol sodium salt.

| Compound 6 | Delmopinol Na Salt | |
|---|---|---|
| Mass (g) | Mass (g) | Comments/Analysis |
| 10.0 | 18.0 | Solvent was distilled at 40° C. Applied the lyophilizer to give the solid. HPLC purity: 98.08% |
| 8.0 | 12.8 | Solid was isolated, HPLC purity: 96.05% |
| 7.4 | 12.0 | Isolated salt HPLC purity: 97.02% |
| 18.0, 12.8, & 12.0 | 40.0 | Isolated salt HPLC purity: 96.9% |

All the reactions were carried out under nitrogen atmosphere. Laboratory grade reagents were purchased and were used as received. Deionized water (DI water) was used for workups and to prepare dilute solutions. $^1$H NMR and $^{13}$C NMR spectra were obtained on a Bruker AVANCE 400 Ultra Shield spectrometer at 400 MHz (for $^1$H NMR) and 100 MHz (for $^{13}$C NMR) with tetramethylsilane used as an internal reference. Thin Layer chromatography (TLC) was performed using Whatman No. 4500-101 (Diamond No. MK6F silica-gel 60 Å) plates. HPLC analyses were performed on an Agilent 1100 Series Instrument. The mass spectra were obtained on a Finnegan LCQ-DUO spectrometer using electrospray ionization.

TABLE 14

HPLC method conditions for delmopinol sodium salt

| Instrument | Agilent HPLC 1290 Infinity Series |
|---|---|
| CAD | Thermo Fischer Corona Veo RS |
| Column | Sunfire C18 (150 × 4.6 mm, 3.5 μm) |
| Column Temperature | 25° C. |
| Auto sampler Temperature | Ambient |
| Detector | CAD |
| Mobile Phases | A: 25 mM ammonium acetate in water B: Acetonitrile Methanol (50:50 % v/v) |
| Flow Rate | 1.0 mL/min |
| Elution | Gradient |

| Time (min) | % A | % B |
|---|---|---|
| 0 | 70 | 30 |
| 5 | 70 | 30 |
| 20 | 20 | 80 |
| 30 | 20 | 80 |
| 30.1 | 70 | 30 |
| 35 | 70 | 30 |

| Injection volume | 5 μL |
|---|---|
| Run time | 35 min |
| Diluent | Acetonitrile:Water (50:50, % v/v) |
| Needle wash | Diluent |

TABLE 15

HPLC method conditions for delmopinol calcium salt

| Instrument | Agilent HPLC 1290 Infinity Series |
|---|---|
| CAD | Thermo Fischer Corona Veo RS |
| Column | Sunfire C18 (150 × 4.6 mm, 3.5 μm) |
| Column Temperature | 25° C. |
| Auto sampler Temperature | Ambient |
| Detector | CAD |
| Mobile Phases | A: 25 mM ammonium acetate in water B: Acetonitrile Methanol (50:50 % v/v) |
| Flow Rate | 1.0 mL/min |
| Elution | Gradient |

TABLE 15-continued

HPLC method conditions for delmopinol calcium salt

| Time (min) | % A | % B |
|---|---|---|
| 0 | 70 | 30 |
| 5 | 70 | 30 |
| 20 | 20 | 80 |
| 30 | 20 | 80 |
| 30.1 | 70 | 30 |
| 35 | 70 | 30 |

| | |
|---|---|
| Injection volume | 5 µL |
| Run time | 35 min |
| Diluent | Acetonitrile:Water (50:50, % v/v) |
| Needle wash | Diluent |

Preparation of compound 2. The solution of 4-heptanone (1200 g, 3.50 mol, Angene Internatioal #AGN2018-3288-1) in dry THF (10800 mL, 9.00 vol, Jet Life Sciences, #THYF001042018) was slowly charged to a solution of allyl magnesium bromide (1 M) in THF (15760 mL, 1.5 equiv, New Age Lifesciences #PO410905) at 25° C. (slight isotherm was observed). Upon addition, the mixture was maintained at 30° C. for 12 h. Progress of the reaction was monitored by TLC using 5% MeOH:$CH_2Cl_2$. The reaction mixture was poured in a premixed solution of ice (1680 g, 1.4 vol), $NH_4Cl$ (20%, 4800 mL, 4.00 vol) and HCl (5 M, 3600 mL, 3.00 vol). The organic phase was separated and the water phase was extracted with MTBE (3×3000 mL). The combined organic phases were dried over anyhydrous $Na_2SO_4$ and evaporated. The resultant crude compound was purified by column chromatography by using silica gel (100-200 mesh) and eluted with 3% MeOH: $CH_2Cl_2$ to afford Compound 2 [1160 g, yield: 70.7%) as slight yellow liquid.

Preparation of compound 3. Hydrogen peroxide 35% solution in water (1087.0 mL, 9.596 mol) was slowly charged to a stirred mixture of morpholine (417.9 g, 4.798 mol), methanol (1250 mL, 5.00 vol), ethanol (1250 mL, 5.00 vol), 4-hydroxy-4-propyl-1-heptene (250 g, 1.60 mol) and $Na_2WO_4.2H_2O$ (52.7 g, 0.1599 mol, 0.1 equiv) at 40-60° C. temperature over a period of 3 h. The resulted mixture was stirred for 18 h at 50-60° C. Progress of the reaction was monitored by TLC using 5% MeOH:$CH_2Cl_2$. Upon completion of reaction, the reaction mixture was cooled to 25° C. and diluted with EtOAc (1000 mL, 4.00 vol) and brine (1000 mL, 4.00 vol). The organic phase was separated and the aqueous phase was extracted with EtOAc (2×1000 mL). The combined organic phase was treated with HCl (5 M, 2000 mL, 8.0 vol). The aqueous phase was adjusted to pH~14 by using sodium hydroxide (6 N, 3000 mL, 12.0 vol) and extracted with EtOAc (3×2000 mL). The organic phase was dried over anhydrous $Na_2SO_4$ and evaporated the solvent to obtain crude compound. Crude compound was purified by column chromatography on silica gel (100-200 mesh) and eluted with 4% MeOH:$CH_2C_2$ to afford Compound 3 (55.0 g, yield: 14.5%) as pale yellow oil.

Preparation of Compound 5. Compound 3 (120 g, 0.466 mol) was charged with p-toluene sulfonic acid (323 g, 1.701 mol), Pd/C (18.0 g, 10%) and isopropanol (840 mL, 7.00 vol) in a autoclave (5.0 L). Hydrogen pressure was applied (50 kg/cm$^2$) at 25° C., the reaction mass was heated at 70-80° C. and maintained for 15 h. Progress of the reaction was monitored by bit mass to know the absence of compound 3 and the formation of compound 5. The reaction mixture was cooled to room temperature and filtered through celite bed. Isopropanol was evaporated under vacuum at 40° C. The crude compound was diluted with NaOH solution (6 M) and extracted with EtOAc (3×600 mL). The organic layer was dried over anhydrous sodium sulphate and concentrate to obtain crude compound 5. The crude was purified by silica gel column (100-200 mesh) using 4% MeOH in $CH_2Cl_2$ to afford pure Compound 5 (39.0 g, yield: 32%) as pale yellow oil.

Preparation of Compound 6. A mixture of compound 5 (100 g, 0.44 mol), chloroethanol (141.7 g, 0.1.76 mol), potassium iodide (43.8 g, 0.26 mol) and ethanol (300 mL, 3.00 vol) was refluxed for 5 h. KOH (22.2 g, 0.395 mol) in ethanol (100 mL, 1.0 vol) was added to the reaction mixture and continued refluxed for 2 h and another KOH (11.1 g, 0.197 mol) in ethanol (50 mL, 0.50 vol) was added to the reaction mixture. The resulted reaction mixture was refluxed for 1 h. Third lot of KOH (9.00 g, 0.160 mol) in ethanol (50 mL, 0.5 vol) was added at 75° C. The reaction mixture was agitated for another 15 h at 75° C. Progress of the reaction was monitored by TLC using 10% MeOH:$CH_2Cl_2$. The solvent was evaporated at 40° C. and water (200 mL) was added to the resulting mixture. The resulting mixture was extracted with EtOAc (3×500 mL), combined organic phases washed with brine (1×100 mL) and dried over anhydrous sodium sulphate. The organic phase was concentrated to obtain 150 g of crude compound 6 (crude Delmopinol). The resultant crude compound was purified by silica gel (100-200 mesh) and eluted with 1% methanol in CH2Cl2 to afford Compound 6 (54.0 g, yield: 45.2%, purity 94.6%). Repurification was performed by using amino silica gel (Cromotex NHDM1020) by taking compound 6 (22.0 g, AMRI lot #IN-SPM-C-203) and eluted with 10% $CH_2Cl_2$ in hexane to afford pure Compound 6 (16.0 g, purity 96.2%) as pale yellow oil.

Preparation of Compound 7 (Delmopinol Calcium salt). Compound 7 (16.0 g, 0.0589 mol) was charged in ethanol (160 mL, 10 vol, OASIS International Services) at room temperature and cooled to 0° C. under nitrogen condition. Calcium chloride (6.50 g, 0.058 mol) was added to the reaction mixture portionwise at 0° C. The resulted reaction mixture was stirred for 1 h at room temperature. The solvents were distilled completely and co-distilled with hexane (2×160 mL). The compound was dried under vacuum to afford Delmopinol Calcium salt (19.0 g, purity 95.7%) as a pale pink solid.

Blending of Delmopinol Calcium salt. Different lots of Delmopinol salt [7.00 g, 12.0 g, 4.00 g, and 21.0 g] were blended to afford a single lot (40.0 g, HPLC purity: 96.1%, AMRI lot #IN-KVK-D-144-1) as a pale pink solid.

Preparation of Compound 7 (Delmopinol sodium salt). Compound 6 (10.0 g, 0.036 mol) was charged in ethanol (100 mL, 10 vol, OASIS International Services) under inert atmosphere. Sodium carbonate (11.7 g, 0.110 mol, 3.00 equiv) was added to the reaction mixture portionwise over a period of 20 min. The resulted reaction mixture was stirred for 2 h at room temperature. The solvents were distilled completely and codistilled with hexane (2×160 mL). The compound was dried by lyophilization to afford Delmopinol Sodium salt (18.0 g, purity 98.1%) as a white solid.

Blending of Delmopinol Sodium salt. Different lots of Delmopinol salt [18.0 g, 16.0 g, and 15.0 g] were blended to afford a single lot (40.0 g, HPLC purity: 96.9%) as a white solid.

Although the present disclosure has been described with respect to one or more particular examples, it will be understood that other examples of the present disclosure may be made without departing from the scope of the present disclosure.

The invention claimed is:

1. A method of making a delmopinol salt, comprising:
contacting

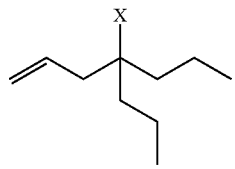

with a first reaction mixture comprising:
 morpholine,
 a first solvent,
 $H_2O_2$, and
 $Na_2WO_4 \cdot 2H_2O$,
wherein

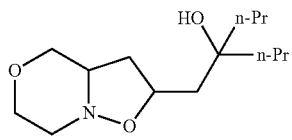

is formed and X is an alcohol or protected alcohol;
contacting the

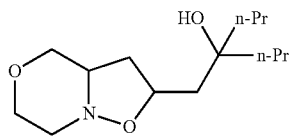

with a second reaction mixture comprising:
 p-toluenesulfonic acid,
 a second solvent,
 $H_2$ gas at a pressure of at least 10 kg/cm², and
 Pd/C,
wherein

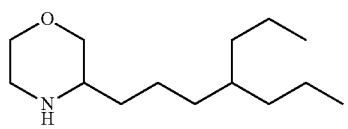 [SMILES: CCCC(CCC)CCCC1COCCN1]

is formed;
contacting the

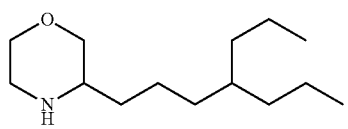 [SMILES: CCCC(CCC)CCCC1COCCN1]

with a third reaction mixture comprising:
 a third solvent,
 a salt,
 a halogenated ethyl alcohol, ethylene oxide, or a halogenated ethane having a protected alcohol, and
 optionally, a base,
wherein

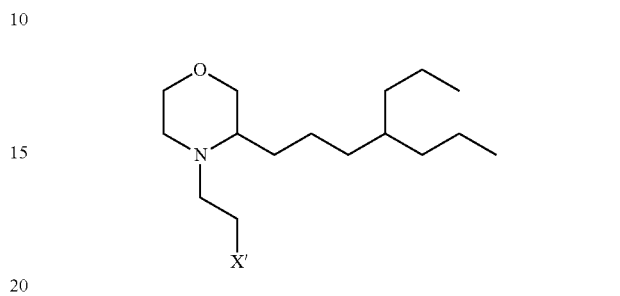

is formed and X' is an alcohol, protected alcohol, or halogen, and
contacting the

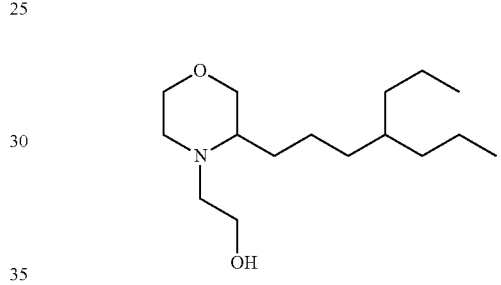

with a metal salt,
wherein

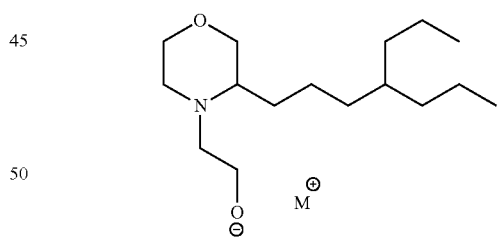

is formed and M⁺ is a metal cation,
with the proviso that the method does not comprise formation of

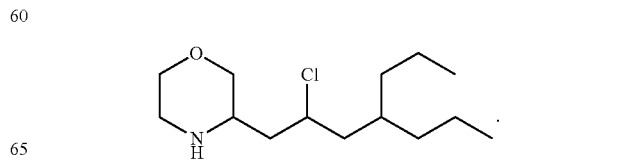

2. The method of claim 1, further comprising removing the protecting group of the protected alcohol after the

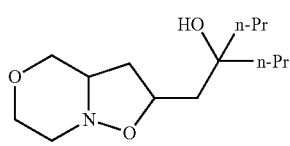

and/or the

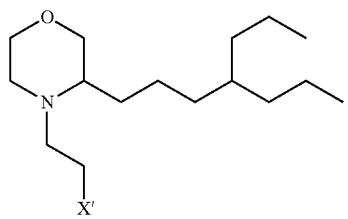

is/are formed.

3. The method of claim 1, wherein the first solvent is an alcohol chosen from ethanol, methanol, and a mixture thereof; acetic acid; or water.

4. The method of claim 1, wherein the second solvent is an alcohol chosen from ethanol, methanol, and a mixture thereof; acetic acid; or water.

5. The method claim 1, wherein the third solvent is an alcohol chosen from methanol, ethanol, and isopropanol; acetic acid; or water.

6. The method of claim 1, wherein the base is chosen from KOH, NaOH, NaH, CaH$_2$ n-BuLi, and s-BuLi.

7. The method of claim 1, wherein the salt is chosen from KI, NaI, tetrabutylammonium iodide (TBAI), and tetrabutylammonium bromide (TBAB).

8. The method of claim 1, wherein the metal salt chosen from sodium salts, potassium salts, magnesium salts, and calcium salts.

9. The method of claim 1, wherein the metal salt is chosen from sodium carbonate, potassium carbonate, magnesium chloride and calcium chloride.

10. The method of claim 1, wherein

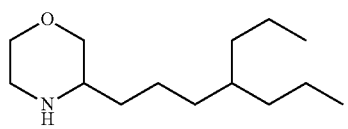 [SMILES: CCCC(CCC)CCCC1COCCN1]

is formed in one step.

11. The method of claim 10, wherein the contacting the

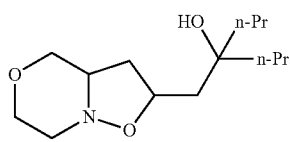

comprises pressurizing to at least 50 kg/cm$^2$.

12. The method of claim 1, wherein

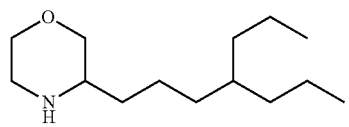 [SMILES: CCCC(CCC)CCCC1COCCN1]

is formed in two steps.

13. The method of claim 12, wherein the first step is contacting the

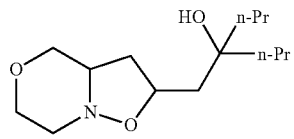

wherein the second reaction mixture further comprising

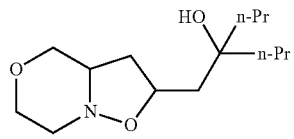

is pressurized to 10-35 kg/cm$^2$.

14. The method of claim 12, wherein the second step comprises contacting the product(s) of the first step to a fourth reaction mixture comprising:
   triphenylphosphine oxide (TPPO);
   triflic anhydride;
   a fourth solvent; and
   a reductant,
wherein

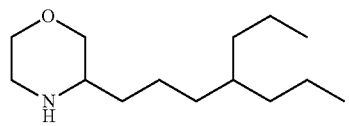 [SMILES: CCCC(CCC)CCCC1COCCN1]

is formed.

15. The method of claim 14, wherein the fourth solvent is chosen from dichloromethane, chloroform, 1,2-dichloroethane, chlorobenzene, and combinations thereof.

16. The method of claim 14, wherein the reductant is chosen from NaBH$_4$, LiBH$_4$, NaBH$_3$CN, LiAlH$_4$, and NaBH(OAc)$_3$.

17. The method of claim 14, wherein the second step comprises:
   i) charging a solution of TPPO in dichloromethane with triflic anhydride at a first temperature to form the fourth reaction mixture;
   ii) adding the products of the first step to the fourth reaction mixture over a first period of time;
   iii) adding NaBH$_4$ to the fourth reaction mixture;
   iv) maintaining the first temperature for a second period of time; and
   v) maintaining the fourth reaction mixture at a second temperature.

18. The method of claim 1, further comprising a workup, isolation, and/or purification step.

19. The method of claim 1, wherein the metal salt is a sodium salt.

20. The method of claim 1, wherein the metal salt is a calcium salt.

* * * * *